(12) United States Patent
Wagner et al.

(10) Patent No.: US 7,928,049 B2
(45) Date of Patent: Apr. 19, 2011

(54) USE OF METAL COMPLEX COMPOUNDS AS OXIDATION CATALYSTS

(75) Inventors: Barbara Wagner, Lörrach (DE); Hauke Rohwer, Lörrach (DE); Marie-Josée Dubs, Wittersdorf (FR); Nicole End, Oberwil (CH); Menno Hazenkamp, Riehen (CH); Sophie Marquais-Bienewald, Hegenheim (FR)

(73) Assignee: BASF SE Ludwigshafen (DE)

( * ) Notice: Subject to any disclaimer, the term of this patent is extended or adjusted under 35 U.S.C. 154(b) by 0 days.

(21) Appl. No.: 12/669,797

(22) PCT Filed: Jul. 14, 2008

(86) PCT No.: PCT/EP2008/059151
§ 371 (c)(1),
(2), (4) Date: Sep. 17, 2010

(87) PCT Pub. No.: WO2009/013163
PCT Pub. Date: Jan. 29, 2009

(65) Prior Publication Data
US 2011/0021407 A1    Jan. 27, 2011

(30) Foreign Application Priority Data
Jul. 23, 2007  (EP) ..................................... 07112912

(51) Int. Cl.
*C11D 1/02*  (2006.01)
*C11D 1/66*  (2006.01)
*C11D 3/28*  (2006.01)
*C11D 3/39*  (2006.01)
*C11D 3/395* (2006.01)

(52) U.S. Cl. ........ 510/311; 510/303; 510/351; 510/356; 510/357; 510/372; 510/376; 510/444; 510/445; 510/500; 510/504; 502/200; 502/324; 502/337; 502/338; 502/345; 502/350

(58) Field of Classification Search .................. 510/303, 510/311, 351, 356, 357, 372, 376, 444, 445, 510/500, 504; 502/200, 324, 337, 338, 345, 502/350
See application file for complete search history.

(56) References Cited

FOREIGN PATENT DOCUMENTS
WO   2004/104155 A1   12/2004
WO   2005/068074 A2   7/2005

OTHER PUBLICATIONS

Zhao et al., Inorganic Chemistry Comm. 9, (2006) pp. 966-968.
Pouralimardan et al., Inorganica Chimica Acta 360 (2007) pp. 1599-1608.

*Primary Examiner* — Gregory R Del Cotto
(74) *Attorney, Agent, or Firm* — Tyler A. Stevenson; Shiela A. Loggins

(57) ABSTRACT

The present invention relates to the use of metal complex compounds having hydrazide ligands as oxidation catalysts. Further aspects of the invention are formulations comprising such metal complex compounds, novel metal complex compounds and novel ligands. The metal complex compounds are used especially for enhancing the action of peroxides, for example in the treatment of textile material, without at the same time causing any appreciable damage to fibers and dyeings. There is also no appreciable damage to fibers and dyeings if these metal complexes are used in combination with an enzyme or a mixture of enzymes.

12 Claims, No Drawings

USE OF METAL COMPLEX COMPOUNDS AS OXIDATION CATALYSTS

The present invention relates to the use of metal complex compounds having hydrazide ligands as oxidation catalysts. Further aspects of the invention are formulations comprising such metal complex compounds, novel metal complex compounds and novel ligands.

The metal complex compounds are used especially for enhancing the action of peroxides, for example in the treatment of textile material, without at the same time causing any appreciable damage to fibres and dyeings. There is also no appreciable damage to fibres and dyeings if these metal complexes are used in combination with an enzyme or a mixture of enzymes.

The metal complex compounds may also be used as catalysts for oxidation using molecular oxygen and/or air, that is, without peroxide compounds and/or peroxide-forming substances. The bleaching of the fabric can happen during and/or after the treatment of the fibre with the formulation, which comprises the metal complexes.

Peroxide-containing bleaching agents have long been used in washing and cleaning processes. They have an excellent action at a liquor temperature of 90° C. and above, but their performance noticeably decreases with lower temperatures. Various transition metal ions added in the form of suitable salts, and coordination compounds containing such cations are known to activate $H_2O_2$. In that manner it is possible for the bleaching effect, which is unsatisfactory at lower temperatures, of $H_2O_2$ or precursors that release $H_2O_2$ and of other peroxo compounds, to be increased. They are important for practical purposes, in that respect, especially combinations of transition metal ions and ligands of which the peroxide activation is manifested in an increased tendency towards oxidation in relation to substrates and not only in a catalase-like disproportionation. The latter activation, which in the present case tends rather to be undesirable, could even impair the bleaching effects, which are inadequate at low temperatures, of $H_2O_2$ and its derivatives.

In terms of $H_2O_2$ activation having effective bleaching action, mononuclear and polynuclear variants of manganese complexes having various ligands, especially 1,4,7-trimethyl-1,4,7-triazacyclononane and optionally oxygen-containing bridging ligands, are currently regarded as being especially effective. Such catalysts are adequately stable under practical conditions and, with $Mn^{n+}$, contain an ecologically acceptable metal cation, but their use is unfortunately associated with considerable damage to dyes and fibres.

The aim of the present invention was accordingly to provide improved metal complex catalysts for oxidation processes that meet the above requirements and, especially, enhance the action of peroxide compounds in the most varied fields of application without causing any appreciable damage.

One aspect of the invention is the use, as a catalyst for oxidation reactions, of at least one metal complex of formula (1)

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y), and
L is a ligand of formula (2)

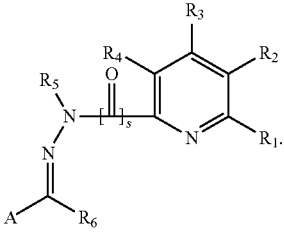

wherein:
s=0 or 1;
A denotes

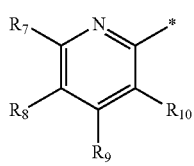

or

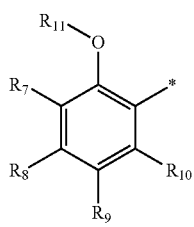

or

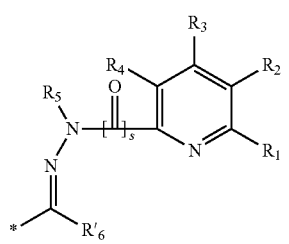

or

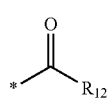

$R_6$ denotes A or hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl or heteroaryl, or OH;
$R'_6$ denotes hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl or heteroaryl, or OH;

* signifies the bond/linkage to the structure of formula (2);

$R_1$ denotes

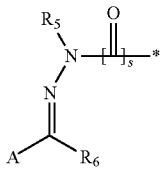

or hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl; cyano; halogen; nitro; or unsubstituted or substituted aryl; or unsubstituted or substituted heteroaryl; —$COOR_{13}$ or —$SO_3R_{13}$ wherein $R_{13}$ is in each case hydrogen, a cation or unsubstituted or substituted $C_1$-$C_{18}$alkyl or unsubstituted or substituted aryl;

—$SR_{14}$—$SO_2R_{14}$ or —$OR_{14}$ wherein $R_{14}$ is in each case hydrogen or unsubstituted or substituted $C_1$-$C_{18}$alkyl or unsubstituted or substituted aryl;

—$NR_{15}R_{16}$; —($C_1$-$C_6$alkylene)-$NR_{15}R_{16}$; —$N^{\oplus}R_{15}R_{16}R_{17}$; —($C_1$-$C_6$alkylene)-$N^{\oplus}R_{15}R_{16}R_{17}$; —$N(R_{14})$—($C_1$-$C_6$alkylene)-$NR_{15}R_{16}$; —$N[(C_1$-$C_6$alkylene)-$NR_{15}R_{16}]_2$; —$N(R_{14})$—($C_1$-$C_6$alkylene)-$N^{\oplus}R_{15}R_{16}R_{17}$; —$N[(C_1$-$C_6$alkylene)-$N^{\oplus}R_{15}R_{16}R_{17}]_2$; —$N(R_{14})$—N—$R_{15}R_{16}$ or —$N(R_{14})$—$N^{\oplus}RR_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms, $R_7$ denotes

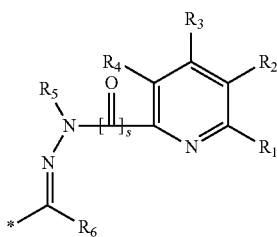

or hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl; cyano; halogen; nitro; —$COOR_{13}$ or —$SO_3R_{13}$ wherein $R_{13}$ is in each case hydrogen, a cation or unsubstituted or substituted $C_1$-$C_{18}$alkyl or unsubstituted or substituted aryl;

—$SR_{14}$, —$SO_2R_{14}$ or —$OR_{14}$ wherein $R_{14}$ is in each case hydrogen or unsubstituted or substituted $C_1$-$C_{18}$alkyl or unsubstituted or substituted aryl;

—$NR_{15}R_{16}$; —($C_1$-$C_6$alkylene)-$NR_{15}R_{16}$; —$N^{\oplus}R_{15}R_{16}R_{17}$; —($C_1$-$C_6$alkylene)-$N^{\oplus}R_{15}R_{16}R_{17}$; —$N(R_{14})$—($C_1$-$C_6$alkylene)-$NR_{15}R_{16}$; —$N[(C_1$-$C_6$alkylene)-$NR_{15}R_{16}]_2$; —$N(R_{14})$—($C_1$-$C_6$alkylene)-$N^{\oplus}R_{15}R_{16}R_{17}$; —$N[(C_1$-$C_6$alkylene)-$N^{\oplus}R_{15}R_{16}R_{17}]_2$; —$N(R_{14})$—$N^{61}$ $R_{15}R_{16}$ or —$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms;

* signifies the bond/linkage to A;

$R_2$, $R_3$, $R_4$, $R_8$, $R_9$, $R_{10}$, $R_{18}$, $R_{19}$, $R_{20}$, $R_{21}$, $R_{22}$, $R_{23}$, $R_{24}$, $R_{25}$, $R_{26}$, and $R_{27}$ are each independently of the others hydrogen; unsubstituted or substituted $C_1$-$C_{18}$alkyl, $C_2$-$C_{28}$alkenyl, $C_3$-$C_{12}$cycloalkyl, $C_3$-$C_{12}$cycloalkenyl or unsubstituted or substituted aryl or unsubstituted or substituted heteroaryl; cyano; halogen; nitro; —OH; —$COOR_{13}$ or —$SO_3R_{13}$ wherein $R_{13}$ is in each case hydrogen, a cation or unsubstituted or substituted $C_1$-$C_{18}$alkyl or unsubstituted or substituted aryl;

—$SR_{14}$, —$SO_2R_{14}$ or —$OR_{14}$ wherein $R_{14}$ is in each case hydrogen or unsubstituted or substituted $C_1$-$C_{18}$alkyl or unsubstituted or substituted aryl;

—$NR_{15}R_{16}$; —($C_1$-$C_6$alkylene)-$NR_{15}R_{16}$; —$N^{\oplus}R_{15}R_{16}R_{17}$; —($C_1$-$C_6$alkylene)-$N^{\oplus}R_{15}R_{16}R_{17}$; —$N(R_{14})$—($C_1$-$C_6$alkylene)-$NR_{15}R_{16}$; —$N[(C_1$-$C_6$alkylene)-$NR_{15}R_{16}]_2$; —$N(R_{14})$—($C_1$-$C_6$alkylene)-$N^{\oplus}R_{15}R_{16}R_{17}$; —$N[(C_1$-$C_6$alkylene)-$N^{\oplus}R_{15}R_{16}R_{17}]_2$; —$N(R_{14})$—N—$R_{15}R_{16}$ or —$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms, $R_5$, $R_{11}$ and $R_{12}$ denote independently of each other hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl, or unsubstituted or substituted heteroaryl;

or $R^1$ and $R^2$, and/or $R^7$ and $R^8$ are a group

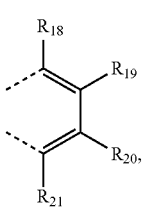

or

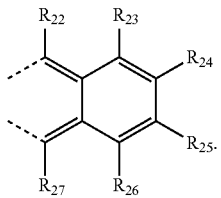

Preferably s is 1.

Compounds in which $R_6$ signifies OH can be also present in their corresponding keto-form.

The ligand L may also be in its protonated or deprotonated analogue form.

Where applicable the acyl hydrazone derivatives can be in their E- or Z-configuration.

Also in the following structures * signifies the bond/linkage from the group A to the structure of formula (2) or where applicable from the structure of formula (2) to the group A.

Suitable substituents for the alkyl groups, aryl groups, alkylene groups or 5-, 6- or 7-membered rings are especially $C_1$-$C_4$alkyl; $C_1$-$C_4$alkoxy; hydroxy; sulfo; sulfato; halogen; cyano; nitro; carboxy; amino; N-mono- or N,N-di-$C_1$-$C_4$alkylamino unsubstituted or substituted by hydroxy in the alkyl moiety; N-phenylamino; N-naphthylamino; phenyl; phenoxy or naphthyloxy.

The $C_1$-$C_{18}$alkyl radicals mentioned for the compounds of formula (2) are, for example, straight-chain or branched alkyl radicals, such as methyl, ethyl, n-propyl, isopropyl, n-butyl, sec-butyl, isobutyl, tert-butyl or straight-chain or branched pentyl, hexyl, heptyl or octyl. Preference is given to $C_1$-$C_{12}$alkyl radicals, especially $C_1$-$C_8$alkyl radicals and preferably $C_1$-$C_4$alkyl radicals. The mentioned alkyl radicals may be unsubstituted or substituted e.g. by hydroxy, $C_1$-$C_4$alkoxy, sulfo or by sulfato, especially by hydroxy. The corresponding unsubstituted alkyl radicals are preferred. Very special preference is given to methyl and ethyl, especially methyl.

Examples of aryl radicals that come into consideration for the compounds of formula (2) are phenyl or naphthyl each unsubstituted or substituted by $C_1$-$C_4$alkyl, $C_1$-$C_4$alkoxy, halogen, cyano, nitro, carboxy, sulfo, hydroxy, amino, N-mono- or N,N-di-$C_1$-$C_4$alkylamino unsubstituted or substituted by hydroxy in the alkyl moiety, N-phenylamino, N-naphthylamino, wherein the amino groups may be quaternised, phenyl, phenoxy or by naphthyloxy. Preferred substituents are $C_1$-$C_4$alkyl, $C_1$-$C_4$alkoxy, phenyl and hydroxy.

Special preference is given to the corresponding phenyl radicals.

The $C_1$-$C_6$alkylene groups mentioned for the compounds of formula (2) are, for example, straight-chain or branched alkylene radicals, such as methylene, ethylene, n-propylene or n-butylene. $C_1$-$C_4$alkylene groups are preferred. The alkylene radicals mentioned may be unsubstituted or substituted, for example by hydroxy or $C_1$-$C_4$alkoxy.

In the compounds of formulae (1) and (2), halogen is preferably chlorine, bromine or fluorine, with special preference being given to chlorine.

Examples of cations that come into consideration for compounds of formulae (1) and (2) include alkali metal cations, such as lithium, potassium and especially sodium, alkaline earth metal cations, such as magnesium and calcium, and ammonium cations. The alkali metal cations, especially sodium, are preferred.

Suitable metal ions for Me for the compounds of formula (1) are, for example, manganese in oxidation states II-V, titanium in oxidation states III and IV, iron in oxidation states I to IV, cobalt in oxidation states I to III, nickel in oxidation states I to III and copper in oxidation states I to III, with special preference being given to manganese, especially manganese in oxidation states II to IV, preferably in oxidation state II. Also of interest are titanium IV, iron II-IV, cobalt I-III, nickel II-III and copper II-III, especially iron II-IV.

For the radical X for the compounds of formula (1) there come into consideration, for example, $CH_3CN$; $H_2O$; $F^-$; $Cl^-$; $Br^-$; $HOO^-$; $O_2^{2-}$; $O^{2-}$; $R_{101}COO^-$; $R_{101}COO^-$; $LMeO^-$ and $LMeOO^-$, wherein $R_{101}$ is hydrogen, —$SO_3C_1$-$C_4$alkyl or unsubstituted or substituted $C_1$-$C_{18}$alkyl or unsubstituted or substituted aryl, and $C_1$-$C_{18}$alkyl, aryl, L and Me have the definitions and preferred meanings given hereinabove and hereinbelow. Especially preferably, $R_{101}$ is hydrogen; $C_1$-$C_4$alkyl; sulfophenyl or phenyl, especially hydrogen.

As counter-ion Y for the compounds of formula (1) there come into consideration, for example, $R_{102}COO^-$; $ClO_4^-$; $BF_4^-$; $PF_6^-$; $R_{102}SO_3^-$; $R_{102}SO_4^-$; $NO_3^-$; $NO_3^-$; $F^-$; $Cl^-$; $Br^-$ and $I^-$, wherein $R_{102}$ is hydrogen or unsubstituted or substituted $C_1$-$C_{18}$alkyl or unsubstituted or substituted aryl. $R_{102}$ as $C_1$-$C_{18}$alkyl or aryl has the definitions and preferred meanings given hereinabove and hereinbelow. Especially preferably, $R_{102}$ is hydrogen; $C_1$-$C_4$alkyl; phenyl or sulfophenyl, especially hydrogen or 4-sulfophenyl. The charge of the counter-ion Y is accordingly preferably 1- or 2-, especially 1-.

Y can also be a customary organic counter-ion, for example citrate, oxalate or tartrate.

Preferably X is $CH_3CN$, $H_2O$, $F^-$, $Cl^-$, $Br^-$, $HOO^-$, $O_2^{2-}$, $O^{2-}$, $R_{101}COO^-$, $R_{101}O^-$, $LMeO^-$ and $LMeOO^-$, wherein $R_{101}$ is hydrogen, unsubstituted or substituted $C_1$-$C_{18}$alkyl or phenyl; L and Me have the definitions as above; and Y is $R_{102}COO^-$, $ClO_4^-$, $BF_4^-$, $PF_6^-$, $R_{102}SO_3^-$, $R_{102}SO_4^-$, $SO_4^{2-}$, $NO_3^-$, $F^-$, $Cl^-$, $Br^-$ and $I^-$.

For the compounds of formula (1), n is preferably an integer having a value of from 1 to 4, preferably 1 or 2 and especially 1.

For the compounds of formula (1), m is preferably an integer having a value of 1 or 2, especially 1.

For the compounds of formula (1), p is preferably an integer having a value of from 0 to 4, especially 2.

For the compounds of formula (1), z is preferably an integer having a value of from 8- to 8+, especially from 4- to 4+ and especially preferably from 0 to 4+. z is more especially the number 0.

For the compounds of formula (1), q is preferably an integer from 0 to 8, especially from 0 to 4, and is especially preferably the number 0.

For example in formula (2)

$R_1$, $R_2$, $R_3$, $R_4$ independently signify H, OH, —$NR_{15}R_{16}$, $N^{\oplus}R_{15}R_{16}R_{17}$, or $C_1$-$C_{18}$alkyl, s 1, $R_5$ denotes H, $R_6$ denotes H, OH, A, $C_1$-$C_{18}$alkyl, unsubstituted or substituted phenyl;

A dentes

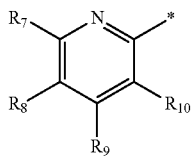

or

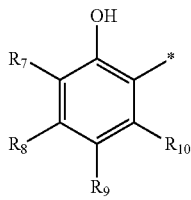

or

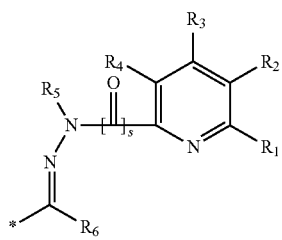

or

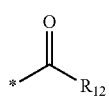

$R_7$, $R_8$, $R_9$, $R_{10}$ and $R_{12}$ are each independently of the other hydrogen, OH, unsubstituted or substituted $C_1$-$C_{18}$alkyl, unsubstituted or substituted aryl, —$NR_{15}R_{16}$; —$N^{\oplus}R_{15}R_{16}R_{17}$;

$R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

For instance in formula (2)

$R_1$, $R_2$, $R_3$, $R_4$ independently signify H, OH, —$NR_{15}R_{16}$, —$N^{\oplus}R_{15}R_{16}R_{17}$, or $C_1$-$C_{18}$alkyl, s 1, $R_5$ denotes H, $R_6$ denotes H, methyl or OH, A denotes

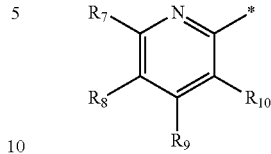

or

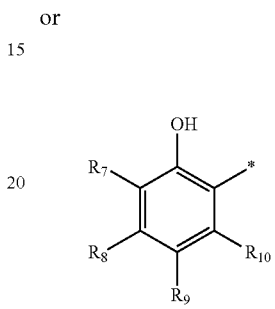

$R_7$, $R_8$, $R_9$, $R_{10}$ are each independently of the other hydrogen, OH, unsubstituted or substituted $C_1$-$C_{18}$alkyl, unsubstituted or substituted phenyl, —$NR_{15}R_{16}$; —$N^{\oplus}R_{15}R_{16}R_{17}$;

$R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms.

Preferably in formula (2)

$R_1$, $R_2$, $R_3$, $R_4$ independently signify H, OH, —$NR_{15}R_{16}$, —$N^{\oplus}R_{15}R_{16}R_{17}$, or $C_1$-$C_{18}$alkyl, s is 1, $R_5$ denotes H, $R_6$ denotes H, methyl, OH, A denotes

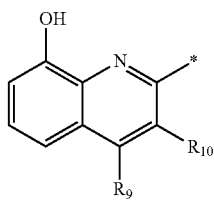

$R_9$, $R_{10}$ are each independently of the other hydrogen, OH, unsubstituted or substituted $C_1$-$C_{18}$alkyl, unsubstituted or substituted phenyl, or —$NR_{15}R_{16}$; —$N^{\oplus}R_{15}R_{16}R_{17}$;

$R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

More preferably formula (2) is of formula (2a)

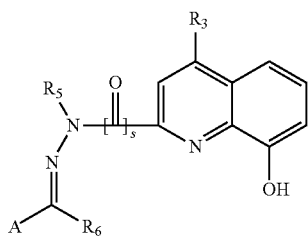

wherein
R$_3$ is H or OH;
s is 1;
R$_5$ denotes H;
R$_6$ denotes A, H, methyl or OH;
A denotes

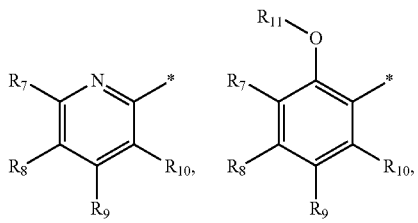

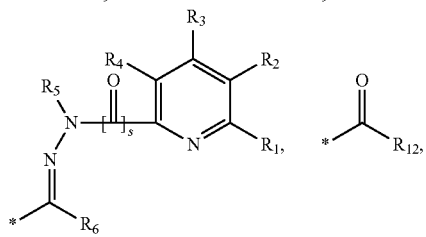

or

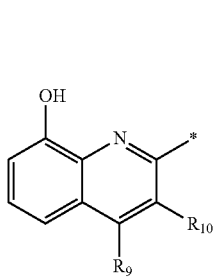

wherein
R$_7$, R$_8$, R$_9$, R$_{10}$, R$_{11}$ and R$_{12}$ are each independently of the other hydrogen, OH, unsubstituted or substituted C$_1$-C$_{18}$alkyl, unsubstituted or substituted phenyl, —NR$_{15}$R$_{16}$; —N$^\oplus$R$_{15}$R$_{16}$R$_{17}$;

R$_{15}$, R$_{16}$ and R$_{17}$ are each independently of the other(s) hydrogen or unsubstituted or substituted C$_1$-C$_{18}$alkyl or unsubstituted or substituted phenyl, or R$_{15}$ and R$_{16}$, together with the nitrogen atom linking them, form an unsubstituted or substituted 5-, 6- or 7-membered ring which may contain further hetero atoms.

Particularly preferred are ligands of formula (2a) wherein

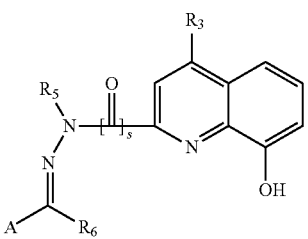

R$_3$ is H or OH;
s is 1,
R$_5$ denotes H;
R$_6$ denotes A, H, methyl or OH;
A denotes

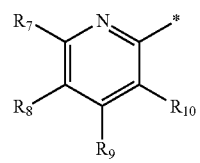

or

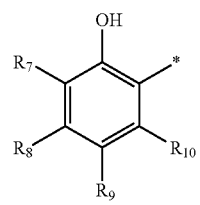

or

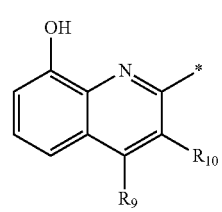

R$_7$, R$_8$, R$_9$, R$_{10}$ are each independently of the other hydrogen, OH, unsubstituted or substituted C$_1$-C$_8$alkyl, unsubstituted or substituted phenyl, —NR$_{15}$R$_{16}$; —N$^\oplus$R$_{15}$R$_{16}$R$_{17}$;

R$_{15}$, R$_{16}$ and R$_{17}$ are each independently of the other(s) hydrogen or unsubstituted or substituted C$_1$-C$_{18}$alkyl or unsubstituted or substituted phenyl, or R$_{15}$ and R$_{16}$, together with the nitrogen atom linking them, form an unsubstituted or substituted 5-, 6- or 7-membered ring which may contain further hetero atoms.

In a specific embodiment of the invention the ligands according to formula (2) correspond to formulae (2b), (2c) or (2d)

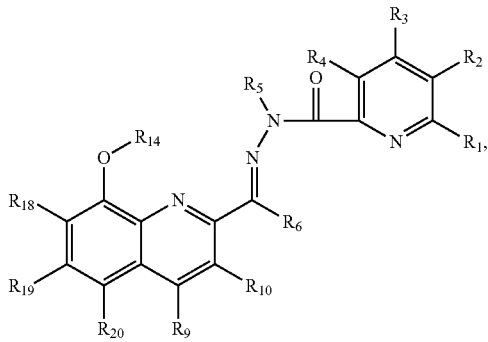

(2b)

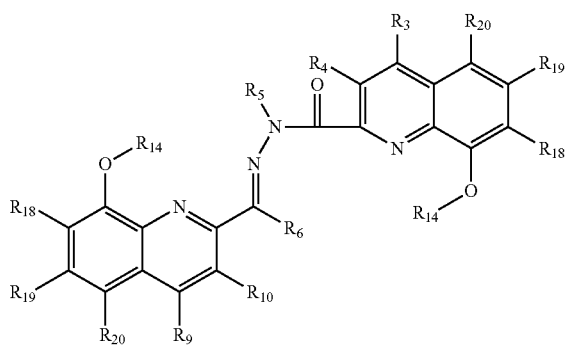

(2c)

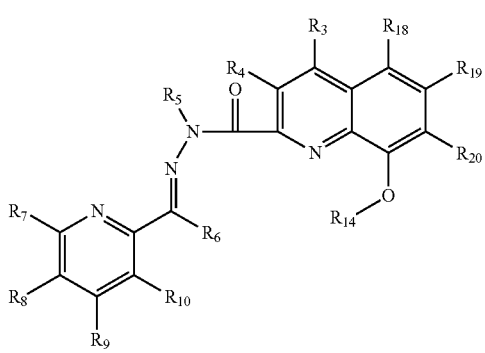

(2d)

wherein
$R_1, R_2, R_3, R_4$ signifies H, OH, —$NR_{15}R_{16}$, —$N^{\oplus}R_{15}R_{16}R_{17}$, or $C_1$-$C_{18}$alkyl,
$R_5$ denotes H,
$R_6$ denotes H, OH, $C_1$-$C_{18}$alkyl, unsubstituted or substituted phenyl;
$R_7, R_8, R_9, R_{10}$ are each independently of the other hydrogen, OH, unsubstituted or substituted $C_1$-$C_8$alkyl, unsubstituted or substituted phenyl, —$NR_{15}R_{16}$; —$N^{\oplus}R_{15}R_{16}R_{17}$;
$R_{15}, R_{16}$ and $R_{17}$ are each independently of the other(s) hydrogen or unsubstituted or substituted $C_1$-$C_{18}$alkyl or unsubstituted or substituted phenyl, or
$R_{15}$ and $R_{16}$, together with the nitrogen atom linking them, form an unsubstituted or substituted 5-, 6- or 7-membered ring which may contain further hetero atoms;
$R_{14}$ is hydrogen or unsubstituted or substituted $C_1$-$C_{18}$alkyl or unsubstituted or substituted phenyl;
$R_{18}, R_{19}$ and $R_{20}$ are independently of each other hydrogen; unsubstituted or substituted $C_1$-$C_{18}$alkyl or unsubstituted or substituted phenyl; cyano; halogen; nitro; —OH; —$COOR_{13}$ or —$SO_3R_{13}$ wherein
$R_{13}$ is hydrogen, a cation or unsubstituted or substituted $C_1$-$C_{18}$alkyl or unsubstituted or substituted aryl;
—$SR_{14}$, —$SO_2R_{14}$ or —$OR_{14}$ wherein
$R_{14}$ hydrogen or unsubstituted or substituted $C_1$-$C_{18}$alkyl or unsubstituted or substituted aryl;
—$NR_{15}R_{16}$; —($C_1$-$C_6$alkylene)-$NR_{15}R_{16}$; —$N^{\oplus}R_{15}R_{16}R_{17}$; —($C_1$-$C_6$alkylene)-$N^{\oplus}R_{15}R_{16}R_{17}$; —$N(R_{14})$—($C_1$-$C_6$alkylene)-$NR_{15}R_{16}$; —$N[(C_1$-$C_6$alkylene)-$NR_{15}R_{16}]_2$; —$N(R_{14})$—($C_1$-$C_6$alkylene)-$N^{\oplus}R_{15}R_{16}R_{17}$; —$N[(C_1$-$C_6$alkylene)-$N^{\oplus}R_{15}R_{16}R_{17}]_2$; —$N(R_{14})$—N—$R_{15}R_{16}$ or —$N(R_{14})$—$N^{\oplus}R_{15}R_{16}R_{17}$, wherein
$R_{14}$ is as defined above and
$R_{15}, R_{16}$ and $R_{17}$ are each independently of the other(s) hydrogen or unsubstituted or substituted $C_1$-$C_{18}$alkyl or unsubstituted or substituted phenyl, or
$R_{15}$ and $R_{16}$, together with the nitrogen atom linking them, form an unsubstituted or substituted 5-, 6- or 7-membered ring which may contain further hetero atoms.

Particularly preferred are ligands of formula (2b).

A preferred embodiment of the present invention relates to the use, as a catalyst for oxidation reactions, of at least one metal complex of formula (1'), $$[L'_n Me'_m X'_p]^{z'} Y'_q \quad (1')$$

wherein
Me' is manganese, titanium, iron, cobalt, nickel or copper,
X' is $CH_3CN$; $H_2O$; $F^-$; $Cl^-$; $Br^-$; $HOO^-$; $O_2^{2-}$; $O^{2-}$; $R_{101}COO^-$; or $R_{101}O^-$, wherein $R_{101}$ is hydrogen, $C_1$-$C_4$alkyl, sulphophenyl or phenyl,
n' is an integer having a value of 1 or 2,
m' is an integer having a value of 1 or 2, preferably 1,
p' is an integer having a value of from 0 to 4, especially 2,
z' is an integer having a value of from 8– to 8+, preferably from 4– to 4+, preferably from 0 to 4+, especially preferably the number 0,
Y' is $R_{102}COO^-$; $ClO_4^-$; $BF_4^-$; $PF_6^-$; $R_{102}SO_3^-$; $R_{102}SO_4^-$; $SO_4^{2-}$; $NO_3^-$; $F^-$; $Cl^-$; $Br^-$, $I^-$, citrate, oxalate or tartrate, wherein $R_{102}$ is hydrogen; $C_1$-$C_4$alkyl; phenyl; or sulfophenyl,
q' is an integer from 0 to 8, preferably from 0 to 4, more preferably the number 0,
L' is a ligand of formula (2b), (2c) or (2d)

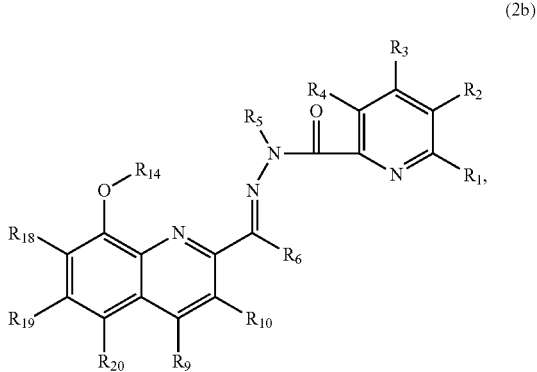

(2b)

-continued

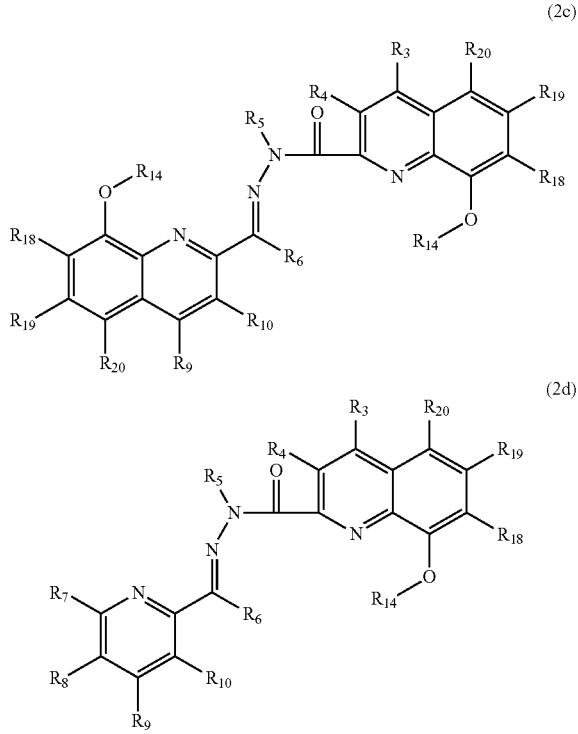

wherein all substituents have the same meanings as defined above.

The majority of the ligands are known and can be prepared according to standard procedures.

The metal complex compounds of formula (1) are used together as catalysts with peroxide or a peroxide-forming substance, $O_2$ and/or air. Examples that may be mentioned in that regard include the following uses:

a) the bleaching of stains or of soiling on textile material in the context of a washing process or by the direct application of a stain remover;
b) the cleaning of hard surfaces, especially kitchen surfaces, wall tiles or floor tiles, for example to remove stains that have formed as a result of the action of moulds ("mould stains"); the use in automatic dishwashing compositions is also a preferred use;
c) the bleaching of stains or of soiling on textile material by atmospheric oxygen, whereby the bleaching is catalysed during and/or after the treatment of the texile in the washing liquor;
d) the prevention of redeposition of migrating dyes during the washing of textile material;
e) use in washing and cleaning solutions having an anti-bacterial action;
f) as pretreatment agents for bleaching textiles;
g) as catalysts in selective oxidation reactions in the context of organic synthesis;
h) waste water treatment;
i) use as a catalyst for reactions with peroxy compounds for bleaching in the context of paper-making. This relates especially to the delignification of cellulose and bleaching of the pulp, which can be carried out in accordance with customary procedures. Also of interest is the use as a catalyst for reactions with peroxy compounds for the bleaching of waste printed paper;
j) sterilisation and
k) contact lens disinfection.

Preference is given to the bleaching of stains or soiling on textile material; to the cleaning of hard surfaces, especially kitchen surfaces, wall tiles, floor tiles as well as the use in automatic dishwasher formulations; to the bleaching of stains or of soiling on textile material by atmospheric oxygen, whereby the bleaching is catalysed during and/or after the treatment of the texile in the washing liquor; or to the prevention of redeposition of migrating dyes in the context of a washing process.

The preferred metals for these uses are manganese and/or iron.

It should be emphasised that the use of metal complex compounds, for example, in the bleaching of textile or hard surface material, does not cause any appreciable damage to fibres and dyeings well as to the hard surface materials, such as table- and kitchen-ware, as well as tiles.

Processes for bleaching stains in any washing liquor are usually carried out by adding to the washing liquor (with $H_2O_2$ or a precursor of $H_2O_2$) one or more metal complex compounds of formula (1) or (1'). Alternatively, it is possible to add a detergent that already comprises one or two metal complex compounds. It will be understood that in such an application, as well as in the other applications, the metal complex compounds of formula (1) or (1') can alternatively be formed in situ, the metal salt (e.g. manganese(II) salt, such as manganese(II) chloride, and/or iron(II) salt, such as iron (II) chloride) and the ligand being added in the desired molar ratios.

Another aspect of the invention is a detergent, cleaning, disinfecting or bleaching composition comprising I) from 0 to 50 wt-%, based on the total weight of the composition, A) of at least one anionic surfactant and/or B) of a non-ionic surfactant,
II) from 0 to 70 wt-%, based on the total weight of the composition, C) of at least one builder substance,
III) 1-99 wt-%, based on the total weight of the composition, D) of at least one peroxide and/or one peroxide-forming substance, $O_2$ and/or air,
IV) E) at least one metal complex compound of formula (1) as defined in claim 1 in an amount that, in the liquor, gives a concentration of from 0.5 to 100 mg/liter of liquor, when from 0.5 to 50 g/liter of the detergent, cleaning, disinfecting or bleaching agent are added to the liquor,
V) 0-20 wt-%, based on the total weight of the composition, of at least one further additive, and
VI) water ad 100 wt-%, based on the total weight of the composition.

Preferably the composition is used for a textile material or a hardsurface material.

All wt-% are based on the total weight of the detergent, cleaning, disinfecting or bleaching composition.

The detergent, cleaning, disinfecting or bleaching composition can be any kind of industrial or domestic cleaning, disinfecting or bleaching formulation.

It can be used for example in compositions used for textile material as well as in composition used for hardsurfaces, such as hard surface materials, such as table- and kitchen-ware, as well as tiles.

Preferred hard surface cleaning compositions are dishwashing detergent formulations, more preferably automatic dishwashing detergent formulations.

The above percentages are in each case percentages by weight, based on the total weight of the composition. The compositions preferably contain from 0.005 to 2 wt-% of at least one metal complex compound of formula (1), more preferably from 0.01 to 1 wt-% and most preferably from 0.05 to 1 wt-%.

Therefore a further embodiment of the present invention relates to a detergent, cleaning, disinfecting or bleaching composition comprising
I) from 0-50 wt-%, preferably from 0-30 wt-% by, A) of at least one anionic surfactant and/or B) of a non-ionic surfactant,
II) from 0-70 wt-%, preferably from 0-50 wt-%, C) of at least one builder substance,
III) from 1-99 wt-%, preferably 1-50 wt-%, D) of at least one peroxide and/or at least one peroxide-forming substance, $O_2$ and/or air,
IV) from 0.005-2 wt-%, more preferably from 0.01-1 wt-% and most preferably from 0.05-1 wt-% E) of at least one metal complex compound of formula (1) or (1') as defined above,
V) from 0-20 wt-% of at least one further additive, and
VI) water ad 100% by weight.

When the compositions according to the invention comprise a component A) and/or B), the amount thereof is preferably from 1 to 50 wt-%, especially from 1 to 30 wt-%.

When the compositions according to the invention comprise a component C), the amount thereof is preferably from 1 to 70 wt-%, especially from 1 to 50 wt-%. Special preference is given to an amount of from 5 to 50 wt-% and especially an amount of from 10 to 50 wt-%.

Corresponding washing, cleaning, disinfecting or bleaching processes are usually carried out by using an aqueous liquor containing from 0.1 to 200 mg of one or more compounds of formula (1) per liter of liquor. The liquor preferably contains from 1 to 50 mg of at least one compound of formula (1) per liter of liquor.

The composition according to the invention can be, for example, a peroxide-containing heavy-duty detergent or a separate bleaching additive, or a stain remover that is to be applied directly. A bleaching additive is used for removing coloured stains on textiles in a separate liquor before the clothes are washed with a bleach-free detergent. A bleaching additive can also be used in a liquor together with a bleach-free detergent.

Stain removers can be applied directly to the textile in question and are used especially for pretreatment in the event of heavy local soiling.

The stain remover can be applied in liquid form, by a spraying method or in the form of a solid substance, such as a powder especially as a granule.

Granules can be prepared, for example, by first preparing an initial powder by spray-drying an aqueous suspension comprising all the components listed above except for component E), and then adding the dry component E) and mixing everything together. It is also possible to add component E) to an aqueous suspension containing components A), B), C) and D) and then to carry out spray-drying.

It is also possible to start with an aqueous suspension that contains components A) and C), but none or only some of component B). The suspension is spray-dried, then component E) is mixed with component B) and added, and then component D) is mixed in the dry state. It is also possible to mix all the components together in the dry state.

The anionic surfactant A) can be, for example, a sulfate, sulfonate or carboxylate surfactant or a mixture thereof. Preference is given to alkylbenzenesulfonates, alkyl sulfates, alkyl ether sulfates, olefin sulfonates, fatty acid salts, alkyl and alkenyl ether carboxylates or to an α-sulfonic fatty acid salt or an ester thereof.

Preferred sulfonates are, for example, alkylbenzenesulfonates having from 10 to 20 carbon atoms in the alkyl radical, alkyl sulfates having from 8 to 18 carbon atoms in the alkyl radical, alkyl ether sulfates having from 8 to 18 carbon atoms in the alkyl radical, and fatty acid salts derived from palm oil or tallow and having from 8 to 18 carbon atoms in the alkyl moiety. The average molar number of ethylene oxide units added to the alkyl ether sulfates is from 1 to 20, preferably from 1 to 10. The cation in the anionic surfactants is preferably an alkaline metal cation, especially sodium or potassium, more especially sodium. Preferred carboxylates are alkali metal sarcosinates of formula $R_{19}$—$CON(R_{20})$$CH_2COOK$ wherein $R_{19}$ is $C_9$-$C_{17}$alkyl or $C_9$-$C_{17}$alkenyl, $R_{20}$ is $C_1$-$C_4$alkyl and $M_1$ is an alkali metal, especially sodium.

The non-ionic surfactant B) may be, for example, a primary or secondary alcohol ethoxylate, especially a $C_8$-$C_{20}$ aliphatic alcohol ethoxylated with an average of from 1 to 20 mol of ethylene oxide per alcohol group. Preference is given to primary and secondary $C_{10}$-$C_{15}$ aliphatic alcohols ethoxylated with an average of from 1 to 10 mol of ethylene oxide per alcohol group. Non-ethoxylated non-ionic surfactants, for example alkylpolyglycosides, glycerol monoethers and polyhydroxyamides (glucamide), may likewise be used.

The total amount of anionic and non-ionic surfactants is preferably from 5 to 50 wt-%, especially from 5 to 40 wt-% and more especially from 5 to 30 wt-%. The lower limit of those surfactants to which even greater preference is given is 10 wt-%.

In addition to anionic and/or non-ionic surfactants the composition may contain cationic surfactants. Possible cationic surfactants include all common cationic surface-active compounds, especially surfactants having a textile softening effect.

Non-limited examples of cationic surfactants are given in the formulas below:

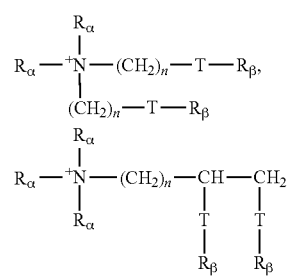

and

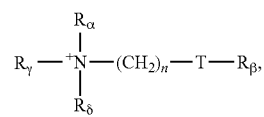

wherein
each radical $R_\alpha$ is independent of the others $C_{1-6}$-alkyl-, -alkenyl- or -hydroxyalkyl; each radical $R_\beta$ is independent of the others $C_{8-28}$-alkyl- or alkenyl;
$R_\gamma$ is $R_\alpha$ or $(CH_2)_n$-T-$R_\beta$;
$R_\delta$ is $R_\alpha$ or $R_\beta$ or $(CH_2)_n$-T-$R_\beta$; T=-$CH_2$—, —O—CO— or —CO—O— and n is between 0 and 5.

Preferred cationic surfactants present in the composition according to the invention include hydroxyalkyl-trialkyl-ammonium-compounds, especially $C_{12-18}$-alkyl(hydroxyethyl) dimethylammonium compounds, and especially preferred the corresponding chloride salts. Compositions of the present invention can contain between 0.5 wt-% and 15 wt-% of the cationic surfactant, based on the total weight of the composition.

As builder substance C) there come into consideration, for example, alkali metal phosphates, especially tripolyphosphates, carbonates and hydrogen carbonates, especially their sodium salts, silicates, aluminum silicates, polycarboxylates, polycarboxylic acids, organic phosphonates, aminoalkylene-poly(alkylenephosphonates) and mixtures of such compounds. Silicates that are especially suitable are sodium salts of crystalline layered silicates of the formula $NaHSi_tO_{2t+1}\cdot pH_2O$ or $Na_2Si_tO_{2t+1}\cdot pH_2O$ wherein t is a number from 1.9 to 4 and p is a number from 0 to 20.

Among the aluminum silicates, preference is given to those commercially available under the names zeolite A, B, X and HS, and also to mixtures comprising two or more of such components. Special preference is given to zeolite A.

Among the polycarboxylates, preference is given to polyhydroxycarboxylates, especially citrates, and acrylates, and also to copolymers thereof with maleic anhydride. Preferred polycarboxylic acids are nitrilotriacetic acid, ethylenediaminetetraacetic acid and ethylene-diamine disuccinate either in racemic form or in the enantiomerically pure (S,S) form.

Phosphonates or aminoalkylenepoly(alkylenephosphonates) that are especially suitable are alkali metal salts of 1-hydroxyethane-1,1-diphosphonic acid, nitrilotris(methylenephosphonic acid), ethylenediaminetetramethylenephosphonic acid and diethylenetriaminepenta-methylenephosphonic acid, and also salts thereof. Also preferred polyphosphonates have the following formula

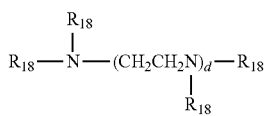

wherein
$R_{18}$ is $CH_2PO_3H_2$ or a water soluble salt thereof and
d is an integer of the value 0, 1, 2 or 3.

Especially preferred are the polyphosphonates wherein b is an integer of the value of 1.

The amount of the peroxide or the peroxide-forming substance is preferably 0.5-30 wt-%, more preferably 1-20 wt-% and especially preferably 1-15 wt-%.

As the peroxide component D) there come into consideration every compound which is capable of yielding hydrogen peroxide in aqueous solutions, for example, the organic and inorganic peroxides known in the literature and available commercially that bleach textile materials at conventional washing temperatures, for example at from 10 to 95° C.

Preferably, however, inorganic peroxides are used, for example persulfates, perborates, percarbonates and/or persilicates.

Example of suitable inorganic peroxides are sodium perborate tetrahydrate or sodium perborated monohydrate, sodium percarbonate, inorganic peroxyacid compounds, such as for example potassium monopersulphate (MPS). If organic or inorganic peroxyacids are used as the peroxygen compound, the amount thereof will normally be within the range of about 2-80 wt-%, preferably from 4-30 wt-%. The organic peroxides are, for example, mono- or poly-peroxides, urea peroxides, a combination of a $C_1$-$C_4$alkanol oxidase and $C_1$-$C_4$alkanol (Such as methanol oxidase and ethanol as described in WO95/07972), alkylhydroxy peroxides, such as cumene hydroperoxide and t-butyl hydroperoxide.

The peroxides may be in a variety of crystalline forms and have different water contents, and they may also be used together with other inorganic or organic compounds in order to improve their storage stability.

All these peroxy compounds may be utilized alone or in conjunction with a peroxyacid bleach precursor and/or an organic bleach catalyst not containing a transition metal. Generally, the bleaching composition of the invention can be suitably formulated to contain from 2 to 80 wt-%, preferably from 4 to 30 wt-%, of the peroxy bleaching agent.

As oxidants, peroxo acids can also be used. One example are organic mono peracids of formula

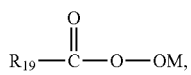

wherein
M signifies hydrogen or a cation,
$R_{19}$ signifies unsubstituted $C_1$-$C_{18}$alkyl; substituted $C_1$-$C_{18}$alkyl; unsubstituted aryl; substituted aryl; —($C_1$-$C_6$alkylene)-aryl, wherein the alkylene and/or the alkyl group may be substituted; and phthalimido$C_1$-$C_8$alkylene, wherein the phthalimido and/or the alkylene group may be substituted.

Preferred mono organic peroxy acids and their salts are those of formula

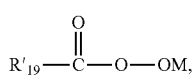

wherein
M signifies hydrogen or an alkali metal, and
$R'_{19}$ signifies unsubstituted $C_1$-$C_4$alkyl; phenyl; —$C_1$-$C_2$alkylene-phenyl or phthalimido$C_1$-$C_8$alkylene.

Especially preferred is $CH_3COOOH$ and its alkali salts.

Especially preferred is also ε-phthalimido peroxy hexanoic acid and its alkali salts.

Also suitable are diperoxyacids, for example, 1,12-diperoxydodecanedioic acid (DPDA), 1,9-diperoxyazelaic acid, diperoxybrassilic acid, diperoxysebasic acid, diperoxyisophthalic acid, 2-decyldiperoxybutane-1,4-diotic acid and 4,4'-sulphonylbisperoxybenzoic acid.

Instead of the peroxy acid it is also possible to use organic peroxy acid precursors and $H_2O_2$. Such precursors are the corresponding carboxyacid or the corresponding carboxyanhydrid or the corresponding carbonylchlorid, or amides, or esters, which can form the peroxy acids on perhydrolysis. Such reactions are commonly known.

Peroxyacid bleach precursors are known and amply described in literature, such as in the British Patents 836988; 864,798; 907,356; 1,003,310 and 1,519,351; German Patent 3,337,921; EP-A-0185522; EP-A-0174132; EP-A-0120591; and U.S. Pat. Nos. 1,246,339; 3,332,882; 4,128,494; 4,412,934 and 4,675,393.

Peroxy acids precursers are often referred to as bleach activators. Suitable bleach activators include the bleach activators, that carry O- and/or N-acyl groups and/or unsubstituted or substituted benzoyl groups. Preference is given to polyacylated alkylenediamines, especially tetraacetylethylenediamine (TAED); acylated glycolurils, especially tetraacetyl glycol urea (TAGU), N,N-diacetyl-N,N-dimethylurea (DDU); sodium-4-benzoyloxy benzene sulphonate (SBOBS); sodium-1-methyl-2-benzoyloxy benzene-4-sulphonate; sodium-4-methyl-3-benzoloxy benzoate; trimethyl ammonium toluoyloxy-benzene sulphonate; acylated triazine derivatives, especially 1,5-diacetyl-2,4-dioxohexahydro-1,3,5-triazine (DADHT); compounds of formula (6):

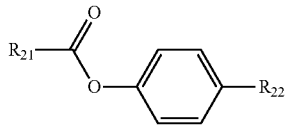
(6)

wherein $R_{22}$ is a sulfonate group, a carboxylic acid group or a carboxylate group, and wherein $R_{21}$ is linear or branched $(C_7-C_{15})$alkyl, especially activators known under the names SNOBS, SLOBS and DOBA; acylated polyhydric alcohols, especially triacetin, ethylene glycol diacetate and 2,5-diacetoxy-2,5-dihydrofuran; and also acetylated sorbitol and mannitol and acylated sugar derivatives, especially pentaacetylglucose (PAG), sucrose polyacetate (SUPA), pentaacetylfructose, tetraacetylxylose and octaacetyllactose as well as acetylated, optionally N-alkylated glucamine and gluconolactone. It is also possible to use the combinations of conventional bleach activators known from German Patent Application DE-A-44 43 177. Nitrile compounds that form perimine acids with peroxides also come into consideration as bleach activators.

Another useful class of peroxyacid bleach precursors is that of the cationic i.e. quaternary ammonium substituted peroxyacid precursors as disclosed in U.S. Pat. Nos. 4,751,015 and 4,397,757, in EP-A0284292 and EP-A-331,229. Examples of peroxyacid bleach precursors of this class are: 2-(N,N,N-trimethyl ammonium)ethyl sodium-4-sulphonphenyl carbonate chloride—(SPCC), N-octyl,N,N-dimethyl-N10-carbophenoxy decyl ammonium chloride —(ODC), 3-(N,N,N-trimethyl ammonium) propyl sodium-4-sulphophenyl carboxylate and N,N,N-trimethyl ammonium toluoyloxy benzene sulphonate.

A further special class of bleach precursors is formed by the cationic nitriles as disclosed in EP-A-303,520, WO 96/40661 and in European Patent Specification No.'s 458,396, 790244 and 464,880. These cationic nitriles also known as nitril quats have the formula

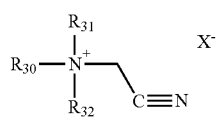
(α)

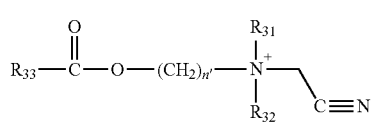
(β)

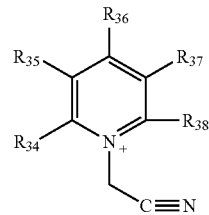
(γ)

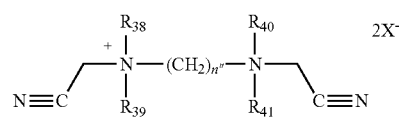
(δ)

wherein $R_{30}$ is a $C_1-C_{24}$alkyl; a $C_1-C_{24}$alkenyl; an alkaryl having a $C_1-C_{24}$alkyl; a substituted $C_1-C_{24}$alkyl; a substituted $C_1-C_{24}$alkenyl; a substituted aryl, $R_{31}$ and $R_{32}$ are each independently a $C_1-C_3$alkyl; hydroxyalkyl having 1 to 3 carbon atoms, —$(C_2H_4O)_n$H, n being 1 to 6; —$CH_2$—CN $R_{33}$ is a $C_1-C_{20}$alkyl; a $C_1-C_{20}$alkenyl; a substituted $C_1-C_{20}$alkyl; a substituted $C_1-C_{20}$alkenyl; an alkaryl having a $C_1-C_{24}$alkyl and at least one other substituent, $R_{34}$, $R_{35}$, $R_{36}$, $R_{37}$ and $R_{38}$ are each independently hydrogen, a $C_1-C_{10}$alkyl, a $C_1-C_{10}$alkenyl, a substituted $C_1-C_{10}$alkyl, a substituted $C_1-C_{10}$alkenyl, carboxyl, sulfonyl or cyano $R_{38}$, $R_{39}$, $R_{40}$ and $R_{41}$ are each independently a $C_1-C_6$alkyl, n' is an integer from 1 to 3, n" is an integer from 1 to 16, and X is an anion.

Other nitril quats have the following formula

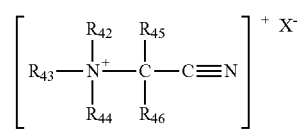
(ε)

wherein $R_{42}$ and $R_{43}$ form, together with the nitrogen atom to which they are bonded, a ring comprising 4 to 6 carbon atoms, this ring may also be substituted by $C_1-C_5$-alkyl, $C_1-C_5$-alkoxy, $C_1-C_5$-alkanoyl, phenyl, amino, ammonium, cyano, cyanamino or chloro and 1 or 2 carbon atom(s) of this ring may also be substituted by a nitrogen atom, by a oxygen atom, by a N—$R_{47}$-group and/or by a $R_{44}$—N—$R_{47}$-group, wherein $R_{47}$ is hydrogen, $C_1-C_5$-alkyl, $C_2-C_5$-alkenyl, $C_2-C_5$-alkinyl, phenyl, $C_7-C_9$-aralkyl, $C_5-C_7$-cycloalkyl, $C_1-C_5$-alkanoyl, cyanomethyl or cyano, $R_{44}$ is $C_1-C_{24}$-, preferably $C_1-C_4$-alkyl; $C_2-C_{24}$-alkenyl, preferably $C_2-C_4$-alkenyl, cyanomethyl or $C_1-C_4$-alkoxy-$C_1$-$C_4$-alkyl, $R_{45}$ and $R_{46}$ are independently from each other hydrogen; $C_1-C_4$-alkyl; $C_1-C_4$-alkenyl; $C_1-C_4$-alkoxy-$C_1$-$C_4$-alkyl; phenyl or $C_1-C_3$-alkylphenyl, preferably hydrogen, methyl or phenyl, whereby preferably the moiety $R_{45}$ signifies hydrogen, if $R_{46}$ is not hydrogen, and $X^-$ is an anion.

Suitable examples of nitril quats of formula (ε) are

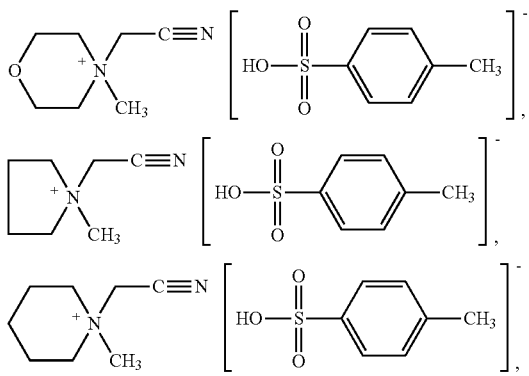

and

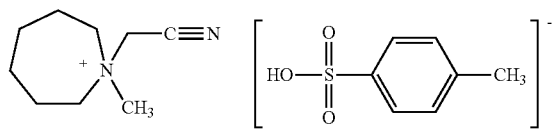

Other nitrile quats have the formula

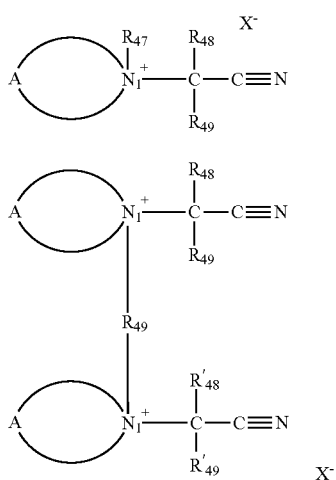

wherein
A is a saturated ring formed by a plurality of atoms in addition to the $N_1$ atom, the saturated ring atoms to include at least one carbon atom and at least one heteroatom in addition to the $N_1$ atom, the said one heteroatom selected from the group consisting of O, S and N atoms, the substituent $R_{47}$ bound to the $N_1$ atom of the Formula (4) structure is (a) a $C_1$-$C_8$-alkyl or alkoxylated alkyl where the alkoxy is $C_{2-4}$, (b) a $C_4$-$C_{24}$cycloalkyl, (c) a $C_7$-$C_{24}$alkaryl, (d) a repeating or non-repeating alkoxy or alkoxylated alcohol, where the alkoxy unit is $C_{2-4}$, or (e) —$CR_{50}R_{51}$—C≡N where $R_{50}$ and $R_{51}$ are each H, a $C_1$-$C_{24}$alkyl, cycloalkyl, or alkaryl, or a repeating or nonrepeating alkoxyl or alkoxylated alcohol where the alkoxy unit is $C_2$-$C_4$, in Formula (φ) at least one of the $R_{48}$ and $R_{49}$ substituents is H and the other of $R_{48}$ and $R_{49}$ is H, a $C_1$-$C_{24}$alkyl, cycloalkyl, or alkaryl, or a repeating or nonrepeating alkoxyl or alkoxylated alcohol where the alkoxy unit is $C_{2-4}$, and Y is at least one counterion.

The precursors may be used in an amount of up to 12 wt-%, preferably from 2-10 wt-% based on the total weight of the composition.

It is also possible to use further bleach catalysts, which are commonly known, for example transition metal complexes as disclosed in EP 1194514, EP 1383857 or WO04/007657.

It is possible to use $H_2O_2$, $O_2$, air, the peroxy-containing compounds, the peroxy-acids as well as their precursors, further bleach catalyst and bleach activists in any combination with the inventive metal complexes.

The compositions may comprise, in addition to the combination according to the invention, one or more optical brighteners, for example from the classes bis-triazinylamino-stilbenedisulfonic acid, bis-triazolyl-stilbenedisulfonic acid, bis-styryl-biphenyl or bis-benzofuranylbiphenyl, α bis-benzoxalyl derivative, bis-benzimidazolyl derivative or coumarin derivative or a pyrazoline derivative.

The compositions may furthermore comprise one or more further additives. Such additives are, for example, dirt-suspending agents, for example sodium carboxymethylcellulose; pH regulators, for example alkali metal or alkaline earth metal silicates; foam regulators, for example soap; salts for adjusting the spray drying and the granulating properties, for example sodium sulfate; perfumes; and also, if appropriate, antistatics and softening agents such as, for example, smectite; bleaching agents; pigments; and/or toning agents. These constituents should especially be stable to any bleaching agent employed.

If the detergent composition is used in an automatic dishwasher it is also common to use silver-corrosion inhibitors.

Such auxiliaries are added in a total amount of from 0.1-20 wt-%, preferably from 0.5-10 wt-%, especially from 0.5-5 wt-%, based on the total weight of the detergent formulation.

Furthermore, the detergent may optionally also comprise enzymes. Enzymes can be added for the purpose of stain removal. The enzymes usually improve the action on stains caused by protein or starch, such as, for example, blood, milk, grass or fruit juices. Preferred enzymes are cellulases and proteases, especially proteases. Cellulases are enzymes that react with cellulose and its derivatives and hydrolyse them to form glucose, cellobiose and celloligosaccharides. Cellulases remove dirt and, in addition, have the effect of enhancing the soft handle of the fabric.

Examples of customary enzymes include, but are by no means limited to, the following: proteases as described in U.S. Pat. No. 6,242,405, column 14, lines 21 to 32; lipases as described in U.S. Pat. No. 6,242,405, column 14, lines 33 to 46; amylases as described in U.S. Pat. No. 6,242,405, column 14, lines 47 to 56; and cellulases as described in U.S. Pat. No. 6,242,405, column 14, lines 57 to 64.

Commercially available detergent proteases, such as Alcalase®, Esperase®, Everlase®, Savinase®, Kannase® and Durazym®, are sold e.g. by NOVOZYMES A/S.

Commercially available detergent amylases, such as Termamyl®, Duramyl®, Stainzyme®, Natalase®, Ban® and Fungamyl®, are sold e.g. by NOVOZYMES A/S.

Commercially available detergent ellulases, such as Celluzyme®, Carezyme® and Endolase®, are sold e.g. by NOVOZYMES A/S.

Commercially available detergent lipases, such as Lipolase®, Lipolase Ultra® and Lipoprime®, are sold e.g. by NOVOZYMES A/S.

Suitable mannanases, such as Mannanaway®, are sold by NOVOZYMES A/S.

Beside in laundry care products, in a hard surface cleaner, especially in a composition used in automatic dishwashers the following enzymes are also commonly used: proteases, amylases, pullulanases, cutinases and lipases, for example proteases such as BLAP®, Optimase®, Opticlean®, Maxacal®, Maxapem®, Esperase® and/or Savinase®, amylases such as Termamyl®, Amylase-LT®, Maxamyl® and/or Duramyl®, lipases such as Lipolase®, Lipomax®, Lumafast® and/or Lipozym®. The enzymes which may be used can, as described e.g. in International Patent Applications WO 92/11347 and WO 94/23005, be adsorbed on carriers and/or embedded in encapsulating substances in order to safeguard them against premature inactivation. They are present in the cleaning formulations according to the invention preferably in amounts not exceeding 5 wt-%, especially in amounts of from 0.1 wt-% to 1.2 wt-%.

Amylases: The present invention preferably makes use of amylases having improved stability in detergents, especially improved oxidative stability. Such amylases are non-limitingly illustrated by the following: (a) An amylase according to WO 94/02597, Novo Nordisk A/S, published Feb. 3, 1994, as further illustrated by a mutant in which substitution is made, using alanine or threonine (preferably threonine), of the methionine residue located in position 197 of the *B. licheniformis* alpha-amylase, known as TERMAMYL®, or the homologous position variation of a similar parent amylase, such as *B. amyloliquefaciens, B. subtilis*, or *B. stearothermophilus*; (b) Stability-enhanced amylases as described by Genencor International in a paper entitled "Oxidatively Resistant alpha-Amylases" presented at the 207th American Chemical Society National Meeting, Mar. 13-17, 1994, by C. Mitchinson. Therein it was noted that bleaches in automatic dishwashing detergents inactivate alpha-amylases but that improved oxidative stability amylases have been made by Genencor from *B. licheniformis* NCIB8061. Any other oxidative stability-enhanced amylase can be used. Proteases: Protease enzymes are usually present in preferred embodiments of the invention at levels between 0.001 wt-% and 5 wt-%. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Suitable commercial proteolytic enzymes include Alcalase®, Esperase®, Durazyme®, Savinase®, Maxatase®, Maxacal®, and Maxapem® 15 (protein engineered Maxacal). Purafect® and subtilisin BPN and BPN' are also commercially available.

When present, lipases comprise from about 0.001 wt-% to about 0.01 wt-% of the instant compositions and are optionally combined with from about 1 wt-% to about 5 wt-% of a surfactant having limesoap-dispersing properties, such as an alkyldimethylamine N-oxide or a sulfobetaine. Suitable lipases for use herein include those of bacterial, animal and fungal origin, including those from chemically or genetically modified mutants.

When incorporating lipases into the instant compositions, their stability and effectiveness may in certain instances be enhanced by combining them with small amounts (e.g., less than 0.5 wt-% of the composition) of oily but non-hydrolyzing materials.

The enzymes, when used, may be present in a total amount of from 0.01 to 5 wt-%, especially from 0.05 to 5 wt-% and more especially from 0.1 to 4 wt-%, based on the total weight of the detergent formulation.

If the detergent formulation is a hard surface cleaning composition, preferably a dishwashing detergent formulation, more preferably an automatic dishwashing detergent formulation, then it can optionally also comprises from about 0.001 wt-% to about 10 wt-%, preferably from about 0.005 wt-% to about 8 wt-%, most preferably from about 0.01 wt-% to about 6 wt-% of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

In order to enhance the bleaching action, the compositions may, in addition to comprising the catalysts described herein, also comprise photocatalysts the action of which is based on the generation of singlet oxygen.

Further preferred additives to the compositions according to the invention are dye-fixing agents and/or polymers which, during the washing of textiles, prevent staining caused by dyes in the washing liquor that have been released from the textiles under the washing conditions. Such polymers are preferably polyvinylpyrrolidones, polyvinylimidazoles or polyvinylpyridine-N-oxides, which may have been modified by the incorporation of anionic or cationic substituents, especially those having a molecular weight in the range of from 5000 to 60 000, more especially from 10 000 to 50 000. Such polymers are usually used in a total amount of from 0.01 to 5 wt-%, especially from 0.05 to 5 wt-%, more especially from 0.1 to 2 wt-%, based on the total weight of the detergent formulation. Preferred polymers are those mentioned in WO-A-02/02865 (see especially page 1, last paragraph and page 2, first paragraph) and those in WO-A-04/05688.

When the inventive detergent composition is used as hard-surface cleaner, especially when the composition is used in automatic dishwasher formulation then, it has been found out, that it is preferable to avoid the use of simple calcium-precipitating soaps as antifoams in the present compositions as they tend to deposit on the dishware. Indeed, phosphate esters are not entirely free of such problems and the formulator will generally choose to minimize the content of potentially depositing antifoams in the instant compositions. Other examples for foam suppressors are paraffin, paraffin/alcohol combinations, or bisfatty acid amides.

The hard surface cleaning compositions, preferably dishwashing detergent formulations, more preferably automatic dishwashing detergent formulations herein may also optionally contain one or more heavy metal chelating agents, such as hydroxyethyldiphosphonate (HEDP). More generally, chelating agents suitable for use herein can be selected from the group consisting of amino carboxylates, amino phosphonates, polyfunctionally-substituted aromatic chelating agents and mixtures thereof. Other suitable chelating agents for use herein are the commercial DEQUEST series, and chelants from Nalco, Inc. Aminocarboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriamine-pentaacetates, and ethanoldiglycines, alkali metal, ammonium, and substituted ammonium salts thereof and mixtures thereof.

Aminophosphonates are also suitable for use as chelating agents in the compositions of the invention when at least low levels of total phosphorus are permitted in detergent compositions, and include ethylenediaminetetrakis (methylenephosphonates).

Preferably, these aminophosphonates do not contain alkyl or alkenyl groups with more than about 6 carbon atoms.

A highly preferred biodegradable chelator for use herein is ethylenediamine disuccinate ("EDDS").

If utilized, these chelating agents or transition-metal selective sequestrants will generally comprise from about 0.001 wt-% to about 10 wt-%, more preferably from about 0.05 wt-% to about 1 wt-% of the hard surface cleaning compositions, preferably dishwashing detergent formulations, more preferably automatic dishwashing detergent formulations herein.

Preferred hard surface cleaning compositions, preferably dishwashing detergent formulations, more preferably automatic dishwashing detergent formulations herein may additionally contain a dispersant polymer. When present, a dispersant polymer is typically at levels in the range from 0 wt-% to about 25 wt-%, preferably from about 0.5 wt-% to about 20 wt-%, more preferably from about 1 wt-% to about 8 wt-% of the detergent composition. Dispersant polymers are useful for improved filming performance of the present dishwasher detergent compositions, especially in higher pH embodiments, such as those in which wash pH exceeds about 9.5. Particularly preferred are polymers, which inhibit the deposition of calcium carbonate or magnesium silicate on dishware.

Suitable polymers are preferably at least partially neutralized or alkali metal, ammonium or substituted ammonium (e.g., mono-, di- or triethanolammonium) salts of polycarboxylic acids. The alkali metal, especially sodium salts are most preferred. While the molecular weight of the polymer can vary over a wide range, it preferably is from about 1,000 to about 500,000, more preferably is from about 1,000 to about 250,000.

Unsaturated monomeric acids that can be polymerized to form suitable dispersant polymers include acrylic acid, maleic acid (or maleic anhydride), fumaric acid, itaconic acid, aconitic acid, mesaconic acid, citraconic acid and methylenemalonic acid. The presence of monomeric segments containing no carboxylate radicals such as methyl vinyl ether, styrene, ethylene, etc. is suitable provided that such segments do not constitute more than about 50 wt-% of the dispersant polymer.

Copolymers of acrylamide and acrylate having a molecular weight of from about 3,000 to about 100,000, preferably from about 4,000 to about 20,000, and an acrylamide content of less than about 50 wt-%, preferably less than about 20 wt-% of the dispersant polymer can also be used. Most preferably, such dispersant polymer has a molecular weight of from about 4,000 to about 20,000 and an acrylamide content of from about 0 wt-% to about 15 wt-%, based on the total weight of the polymer.

Particularly preferred dispersant polymers are low molecular weight modified polyacrylate copolymers. Such copolymers contain as monomer units: a) from about 90 wt-% to about 10 wt-%, preferably from about 80 wt-% to about 20 wt-% acrylic acid or its salts and b) from about 10 wt-% to about 90 wt-%, preferably from about 20 wt-% to about 80 wt-% of a substituted acrylic monomer or its salt and have the general formula:
—[(C(R$_a$)C(R$_b$)(C(O)OR$_c$)] wherein the apparently unfilled valencies are in fact occupied by hydrogen and at least one of the substituents R$_a$, R$_b$, or R$_c$, preferably R$_a$ or R$_b$, is a 1 to 4 carbon alkyl or hydroxyalkyl group; R$_a$ or R$_b$ can be a hydrogen and R$_c$ can be a hydrogen or alkali metal salt. Most preferred is a substituted acrylic monomer wherein R$_a$ is methyl, R$_b$ is hydrogen, and R$_c$ is sodium.

A suitable low molecular weight polyacrylate dispersant polymer preferably has a molecular weight of less than about 15,000, preferably from about 500 to about 10,000, most preferably from about 1,000 to about 5,000. The most preferred polyacrylate copolymer for use herein has a molecular weight of about 3,500 and is the fully neutralized form of the polymer comprising about 70 wt-% acrylic acid and about 30 wt-% methacrylic acid.

Other dispersant polymers useful herein include the polyethylene glycols and polypropylene glycols having a molecular weight of from about 950 to about 30,000.

Yet other dispersant polymers useful herein include the cellulose sulfate esters such as cellulose acetate sulfate, cellulose sulfate, hydroxyethyl cellulose sulfate, methylcellulose sulfate, and hydroxypropylcellulose sulfate. Sodium cellulose sulfate is the most preferred polymer of this group.

Other suitable dispersant polymers are the carboxylated polysaccharides, particularly starches, celluloses and alginates.

Yet another group of acceptable dispersants are the organic dispersant polymers, such as polyaspartate.

Depending on whether a greater or lesser degree of compactness is required, filler materials can also be present in the instant hard surface cleaning compositions, preferably dishwashing detergent formulations, more preferably automatic dishwashing detergent formulations. These include sucrose, sucrose esters, sodium sulfate, potassium sulfate, etc., in amounts up to about 70 wt-%, preferably from 0 wt-% to about 40 wt-% of the hard surface cleaning compositions, preferably dishwashing detergent formulations, more preferably automatic dishwashing detergent formulations. Preferred filler is sodium sulfate, especially in good grades having at most low levels of trace impurities.

Sodium sulfate used herein preferably has a purity sufficient to ensure it is non-reactive with bleach; it may also be treated with low levels of sequestrants, such as phosphonates or EDDS in magnesium-salt form. Note that preferences, in terms of purity sufficient to avoid decomposing bleach, applies also to pH-adjusting component ingredients, specifically including any silicates used herein.

Organic solvents that can be used in the cleaning formulations according to the invention, especially when the latter are in liquid or paste form, include alcohols having from 1 to 4 carbon atoms, especially methanol, ethanol, isopropanol and tert-butanol, diols having from 2 to 4 carbon atoms, especially ethylene glycol and propylene glycol, and mixtures thereof, and the ethers derivable from the mentioned classes of compound. Such water-miscible solvents are present in the cleaning formulations according to the invention preferably in amounts not exceeding 20 wt-%, especially in amounts of from 1 wt-% to 15 wt-%.

Many hard surface cleaning compositions, preferably dishwashing detergent formulations, more preferably automatic dishwashing detergent formulations herein will be buffered, i.e., they are relatively resistant to pH drop in the presence of acidic soils. However, other compositions herein may have exceptionally low buffering capacity, or may be substantially unbuffered. Techniques for controlling or varying pH at recommended usage levels more generally include the use of not only buffers, but also additional alkalis, acids, pH-jump systems, dual compartment containers, etc., and are well known to those skilled in the art.

Certain hard surface cleaning compositions, preferably dishwashing detergent formulations, more preferably automatic dishwashing detergent formulations, comprise a pH-adjusting component selected from water-soluble alkaline inorganic salts and water-soluble organic or inorganic builders. The pH-adjusting components are selected so that when the hard surface cleaning composition, preferably dishwashing detergent formulation, more preferably automatic dishwashing detergent formulation is dissolved in water at a concentration of 1,000-5,000 ppm, the pH remains in the range of above about 8, preferably from about 9.5 to about 11. The preferred nonphosphate pH-adjusting component can be selected from the group consisting of:

(i) sodium carbonate or sesquicarbonate;
(ii) sodium silicate, preferably hydrous sodium silicate having $SiO_2:Na_2O$ ratio of from about 1:1 to about 2:1, and mixtures thereof with limited quantities of sodium metasilicate;
(iii) sodium citrate;
(iv) citric acid;
(v) sodium bicarbonate;
(vi) sodium borate, preferably borax;
(vii) sodium hydroxide; and
(viii) mixtures of (i)-(vii).

Preferred embodiments contain low levels of silicate (i.e. from about 3 wt-% to about 10 wt-% $SiO_2$).

Illustrative of highly preferred pH-adjusting component systems of this specialized type are binary mixtures of granular sodium citrate with anhydrous sodium carbonate, and three-component mixtures of granular sodium citrate trihydrate, citric acid monohydrate and anhydrous sodium carbonate.

The amount of the pH adjusting component in compositions used for automatic dishwashing is preferably from about 1 wt-% to about 50 wt-% of the composition. In a preferred embodiment, the pH-adjusting component is present in the composition in an amount from about 5 wt-% to about 40 wt-%, preferably from about 10 wt-% to about 30 wt-%. For compositions herein having a pH between about 9.5 and about 11 of the initial wash solution, particularly preferred automatic dishwashing detergent formulations embodiments comprise, by weight of the automatic dishwashing detergent formulations, from about 5 wt-% to about 40 wt-%, preferably from about 10 wt-% to about 30 wt-%, most preferably from about 15 wt-% to about 20 wt-%, of sodium citrate with from about 5 wt-% to about 30 wt-%, preferably from about 7 wt-% to 25 wt-%, most preferably from about 8 wt-% to about 20 wt-% sodium carbonate.

The essential pH-adjusting system can be complemented (i.e. for improved sequestration in hard water) by other optional detergency builder salts selected from nonphosphate detergency builders known in the art, which include the various water-soluble, alkali metal, ammonium or substituted ammonium borates, hydroxysulfonates, polyacetates, and polycarboxylates. Preferred are the alkali metals, especially sodium, salts of such materials. Alternate water-soluble, non-phosphorus organic builders can be used for their sequestering properties. Examples of polyacetate and polycarboxylate builders are the sodium, potassium, lithium, ammonium and substituted ammonium salts of ethylenediamine tetraacetic acid; nitrilotriacetic acid, tartrate monosuccinic acid, tartrate disuccinic acid, oxydisuccinic acid, carboxymethoxysuccinic acid, mellitic acid, and sodium benzene polycarboxylate salts.

The detergent formulations can take a variety of physical forms such as, for example, powder granules, tablets (tabs), gel and liquid. Examples thereof include, inter alia, conventional high-performance detergent powders, supercompact high-performance detergent powders and tabs. One important physical form is the so-called concentrated granular form, which is added to a washing machine.

Also of importance are so-called compact or supercompact detergents. In the field of detergent manufacture, there is a trend towards the production of such detergents that contain an increased amount of active substances. In order to minimize energy consumption during the washing procedure, compact or supercompact detergents need to act effectively at low washing temperatures, for example below 40° C., or even at room temperature (25° C.). Such detergents usually contain only small amounts of fillers or of substances, such as sodium sulfate or sodium chloride, required for detergent manufacture. The total amount of such substances is usually from 0 to 10 wt-%, especially from 0 to 5 wt-%, more especially from 0 to 1 wt-%, based on the total weight of the detergent formulation. Such (super)compact detergents usually have a bulk density of from 650 to 1000 g/l, especially from 700 to 1000 g/l and more especially from 750 to 1000 g/l.

The detergent formulations can also be in the form of tablets (tabs). The advantages of tabs reside in the ease of dispensing and convenience in handling. Tabs are the most compact form of solid detergent formulation and usually have a volumetric density of, for example, from 0.9 to 1.3 kg/liter. To achieve rapid dissolution, such tabs generally contain special dissolution aids:

carbonate/hydrogen carbonate/citric acid as effervescents;
disintegrators, such as cellulose, carboxymethyl cellulose or cross-linked poly(N-vinyl-pyrrolidone);
rapidly dissolving materials, such as sodium (potassium) acetates, or sodium (potassium) citrates;
rapidly dissolving, water-soluble, rigid coating agents, such as dicarboxylic acids.

The tabs may also comprise combinations of such dissolution aids.

The detergent formulation may also be in the form of an aqueous liquid containing from 5 wt-% to 50 wt-%, preferably from 10 wt-% to 35 wt-%, of water or in the form of a non-aqueous liquid containing no more than 5 wt-%, preferably from 0 wt-% to 1 wt-% of water. Non-aqueous liquid detergent formulations may comprise other solvents as carriers. Low molecular weight primary or secondary alcohols, for example methanol, ethanol, propanol and isopropanol, are suitable for that purpose. The solubilising surfactant used is preferably a monohydroxy alcohol but polyols, such as those containing from 2 to 6 carbon atoms and from 2 to 6 hydroxy groups (e.g., 1,3-propanediol, ethylene glycol, glycerol and 1,2-propanediol) can also be used. Such carriers are usually used in a total amount of from 5 wt-% to 90 wt-%, preferably from 10 wt-% to 50 wt-%, based on the total weight of the detergent formulation. The detergent formulations can also used in so-called "unit liquid dose" form.

The invention relates also to granules that comprise the catalysts according to the invention and are suitable for incorporation into a powder-form or granular detergent, cleaning or bleaching composition. Such granules preferably comprise:

a) from 1-99 wt-%, based on the total weight of the granule, of at least one metal complex compound of formula (1) as defined and of at least one peroxide,
b) from 1-99 wt-%, based on the total weight of the granule, of at least one binder,
c) from 0-20 wt-%, based on the total weight of the granule, of at least one encapsulating material,
d) from 0-20 wt-%, based on the total weight of the granule, of at least one further additive and
e) from 0-20 wt-% based on the total weight of the granule, of water.

All wt-% are based on the total weight of the granule.

Or as an alternative the granule can comprise a) from 1 wt-% to 99 wt-%, preferably from 1 wt-% to 40 wt-%, especially from 1 wt-% to 30 wt-%, of at least one metal complex compound of formula (1) and of at least one peroxide-forming substance, b) from 1 wt-% to 99 wt-%, preferably from 10 wt-% to 99 wt-%, especially from 20 wt-% to 80 wt-%, of at least one binder, c) from 0 wt-% to 20 wt-%, especially from 1 to 20 wt-%, of at least one encapsulating material, d) from 0 wt-% to 20 wt-% of at least one further additive and e) from 0 wt-% to 20 wt-% water.

All wt-% are based on the total weight of the granule.

For metal complex compounds of formula (1) and the peroxide or the peroxide-forming substances as described above [component a)] all preferences as defined above apply also for the granule. It is also possible to granule the catalyst as such together with suitable granulate material.

As binder (b) there come into consideration water-soluble, dispersible or water-emulsifiable anionic dispersants, non-ionic dispersants, polymers and waxes.

The anionic dispersants used are, for example, commercially available water-soluble anionic dispersants for dyes, pigments etc.

The following products, especially, come into consideration: condensation products of aromatic sulfonic acids and formaldehyde, condensation products of aromatic sulfonic acids with unsubstituted or chlorinated diphenyls or diphenyl oxides and optionally formaldehyde, (mono-/di-)alkylnaphthalenesulfonates, sodium salts of polymerised organic sulfonic acids, sodium salts of polymerised alkylnaphthalenesulfonic acids, sodium salts of polymerised alkylbenzenesulfonic acids, alkylarylsulfonates, sodium salts of alkyl polyglycol ether sulfates, polyalkylated polynuclear arylsulfonates, methylene-linked condensation products of arylsulfonic acids and hydroxyarylsulfonic acids, sodium salts of dialkylsulfosuccinic acid, sodium salts of alkyl diglycol ether sulfates, sodium salts of polynaphthalenemethanesulfonates, lignosulfonates or oxylignosulfonates and heterocyclic polysulfonic acids.

Especially suitable anionic dispersants are condensation products of naphthalenesulfonic acids with formaldehyde, sodium salts of polymerised organic sulfonic acids, (mono-/di-)-alkylnaphthalenesulfonates, polyalkylated polynuclear arylsulfonates, sodium salts of polymerised alkylbenzenesulfonic acid, lignosulfonates, oxylignosulfonates and condensation products of naphthalenesulfonic acid with a polychloromethyldiphenyl.

Suitable non-ionic dispersants are especially compounds having a melting point of, preferably, at least 35° C. that are emulsifiable, dispersible or soluble in water, for example the following compounds:

1. fatty alcohols having from 8 to 22 carbon atoms, especially cetyl alcohol;
2. addition products of, preferably, from 2 to 80 mol of alkylene oxide, especially ethylene oxide, wherein some of the ethylene oxide units may have been replaced by substituted epoxides, such as styrene oxide and/or propylene oxide, with higher unsaturated or saturated monoalcohols, fatty acids, fatty amines or fatty amides having from 8 to 22 carbon atoms or with benzyl alcohols, phenyl phenols, benzyl phenols or alkyl phenols, the alkyl radicals of which have at least 4 carbon atoms;
3. alkylene oxide, especially propylene oxide, condensation products (block polymers);
4. ethylene oxide/propylene oxide adducts with diamines, especially ethylenediamine;
5. reaction products of a fatty acid having from 8 to 22 carbon atoms and a primary or secondary amine having at least one hydroxy-lower alkyl or lower alkoxy-lower alkyl group, or alkylene oxide addition products of such hydroxyalkyl-group-containing reaction products;
6. sorbitan esters, preferably having long-chain ester groups, or ethoxylated sorbitan esters, such as polyoxyethylene sorbitan monolaurate having from 4 to 10 ethylene oxide units or polyoxyethylene sorbitan trioleate having from 4 to 20 ethylene oxide units;
7. addition products of propylene oxide with a tri- to hexa-hydric aliphatic alcohol having from 3 to 6 carbon atoms, e.g. glycerol or pentaerythritol; and
8. fatty alcohol polyglycol mixed ethers, especially addition products of from 3 to 30 mol of ethylene oxide and from 3 to 30 mol of propylene oxide with aliphatic monoalcohols having from 8 to 22 carbon atoms.

Especially suitable non-ionic dispersants are surfactants of formula $$R_{23}\text{—O-(alkylene-O)}_n\text{—}R_{24} \qquad (7),$$

wherein $R_{23}$ is $C_8$-$C_{22}$alkyl or $C_8$-$C_{18}$alkenyl;

$R_{24}$ is hydrogen; $C_1$-$C_4$alkyl; a cycloaliphatic radical having at least 6 carbon atoms; or benzyl;

"alkylene" is an alkylene radical having from 2 to 4 carbon atoms and n is a number from 1 to 60.

The substituents $R_{23}$ and $R_{24}$ in formula (7) are advantageously each the hydrocarbon radical of an unsaturated or, preferably, saturated aliphatic monoalcohol having from 8 to 22 carbon atoms. The hydrocarbon radical may be straight-chain or branched. $R_{23}$ and $R_{24}$ are preferably each independently of the other an alkyl radical having from 9 to 14 carbon atoms.

Aliphatic saturated monoalcohols that come into consideration include natural alcohols, e.g. lauryl alcohol, myristyl alcohol, cetyl alcohol or stearyl alcohol, and also synthetic alcohols, e.g. 2-ethylhexanol, 1,1,3,3-tetramethylbutanol, octan-2-ol, isononyl alcohol, trimethylhexanol, trimethylnonyl alcohol, decanol, $C_9$-$C_{11}$oxo-alcohol, tridecyl alcohol, isotridecyl alcohol and linear primary alcohols (Alfols) having from 8 to 22 carbon atoms. Some examples of such Alfols are Alfol (8-10), Alfol (9-11), Alfol (10-14), Alfol (12-13) and Alfol (16-18). ("Alfol" is a registered trade mark of the company Sasol Limited). Unsaturated aliphatic monoalcohols are, for example, dodecenyl alcohol, hexadecenyl alcohol and oleyl alcohol.

The alcohol radicals may be present singly or in the form of mixtures of two or more components, e.g. mixtures of alkyl and/or alkenyl groups that are derived from soybean fatty acids, palm kernel fatty acids or tallow oils.

(Alkylene-O) chains are preferably bivalent radicals of the formulae —(CH$_2$—CH$_2$—O)—,

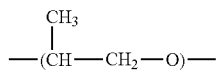

and

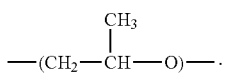

Examples of a cycloaliphatic radical include cycloheptyl, cyclooctyl and preferably cyclohexyl.

As non-ionic dispersants there come into consideration preferably surfactants of formula

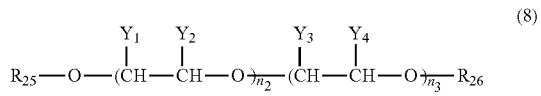

wherein
$R_{25}$ is $C_8$-$C_{22}$alkyl;
$R_{26}$ is hydrogen or $C_1$-$C_4$alkyl;
$Y_1, Y_2, Y_3$ and $Y_4$ are each independently of the others hydrogen, methyl or ethyl;
$n_2$ is a number from 0 to 8; and
$n_3$ is a number from 2 to 40.

Further important non-ionic dispersants correspond to formula

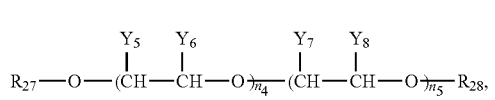

wherein
$R_{27}$ is $C_9$-$C_{14}$alkyl;
$R_{28}$ is $C_1$-$C_4$alkyl;
$Y_5, Y_6, Y_7$ and $Y_8$ are each independently of the others hydrogen, methyl or ethyl, one of the radicals $Y_5, Y_6$ and one of the radicals $Y_7, Y_8$ always being hydrogen; and
$n_4$ and $n_5$ are each independently of the other an integer from 4 to 8.

The non-ionic dispersants of formulae (7) to (9) can be used in the form of mixtures. For example, as surfactant mixtures there come into consideration non-end-group-terminated fatty alcohol ethoxylates of formula (7), e.g. compounds of formula (7) wherein
$R_{23}$ is $C_8$-$C_{22}$alkyl,
$R_{24}$ is hydrogen and
the alkylene-O chain is the radical —$(CH_2$—$CH_2$—O)— and also end-group-terminated fatty alcohol ethoxylates of formula (9).

Examples of non-ionic dispersants of formulae (7), (8) and (9) include reaction products of a $C_{10}$-$C_{13}$fatty alcohol, e.g. a $C_{13}$oxo-alcohol, with from 3 to 10 mol of ethylene oxide, propylene oxide and/or butylene oxide and the reaction product of one mol of a $C_{13}$fatty alcohol with 6 mol of ethylene oxide and 1 mol of butylene oxide, it being possible for the addition products each to be end-group-terminated with $C_1$-$C_4$alkyl, preferably methyl or butyl.

Such dispersants can be used singly or in the form of mixtures of two or more dispersants.

Instead of, or in addition to, the anionic or non-ionic dispersant, the granules according to the invention may comprise a water-soluble organic polymer as binder. Such polymers may be used singly or in the form of mixtures of two or more polymers.

Water-soluble polymers that come into consideration are, for example, polyethylene glycols, copolymers of ethylene oxide with propylene oxide, gelatin, polyacrylates, polymethacrylates, polyvinylpyrrolidones, vinylpyrrolidones, vinyl acetates, polyvinylimidazoles, polyvinylpyridine-N-oxides, copolymers of vinylpyrrolidone with long-chain α-olefins, copolymers of vinylpyrrolidone with vinylimidazole, poly(vinylpyrrolidone/dimethylaminoethyl methacrylates), copolymers of vinylpyrrolidone/dimethylaminopropyl methacrylamides, copolymers of vinylpyrrolidone/dimethylaminopropyl acrylamides, quaternised copolymers of vinylpyrrolidones and dimethylaminoethyl methacrylates, terpolymers of vinylcaprolactam/vinylpyrrolidone/dimethylaminoethyl methacrylates, copolymers of vinylpyrrolidone and methacrylamidopropyl-trimethylammonium chloride, terpolymers of caprolactam/vinylpyrrolidone/dimethylaminoethyl methacrylates, copolymers of styrene and acrylic acid, polycarboxylic acids, polyacrylamides, carboxymethyl cellulose, hydroxymethyl cellulose, polyvinyl alcohols, polyvinyl acetate, hydrolysed polyvinyl acetate, copolymers of ethyl acrylate with methacrylate and methacrylic acid, copolymers of maleic acid with unsaturated hydrocarbons, and also mixed polymerisation products of the mentioned polymers.

Of those organic polymers, special preference is given to polyethylene glycols, carboxymethyl cellulose, polyacrylamides, polyvinyl alcohols, polyvinylpyrrolidones, gelatin, hydrolysed polyvinyl acetates, copolymers of vinylpyrrolidone and vinyl acetate, and also polyacrylates, copolymers of ethyl acrylate with methacrylate and methacrylic acid, and polymethacrylates.

Suitable water-emulsifiable or water-dispersible binders also include paraffin waxes.

Encapsulating materials (c) include especially water-soluble and water-dispersible polymers and waxes. Of those materials, preference is given to polyethylene glycols, polyamides, polyacrylamides, polyvinyl alcohols, polyvinylpyrrolidones, gelatin, hydrolysed polyvinyl acetates, copolymers of vinylpyrrolidone and vinyl acetate, and also polyacrylates, paraffins, fatty acids, copolymers of ethyl acrylate with methacrylate and methacrylic acid, and polymethacrylates.

Further additives (d) that come into consideration are, for example, wetting agents, dust removers, water-insoluble or water-soluble dyes or pigments, and also dissolution accelerators, optical brighteners and sequestering agents.

The preparation of the granules according to the invention is carried out, for example, starting from:
a) a solution or suspension with a subsequent drying/shaping step or
b) a suspension of the active ingredient in a melt with subsequent shaping and solidification.

a) First of all the anionic or non-ionic dispersant and/or the polymer and, optionally, the further additives are dissolved in water and stirred, if desired with heating, until a homogeneous solution is obtained. The catalyst according to the invention is then dissolved or suspended in the resulting aqueous solution. The solids content of the solution should preferably be at least 30 wt-%, especially from 40 wt-% to 50 wt-%, based on the total weight of the solution. The viscosity of the solution is preferably less than 200 mPas.

The aqueous solution so prepared, comprising the catalyst according to the invention, is then subjected to a drying step in which all water, with the exception of a residual amount, is removed, solid particles (granules) being formed at the same time. Known methods are suitable for producing the granules from the aqueous solution. In principle, both continuous methods and discontinuous methods are suitable. Continuous methods are preferred, especially spray-drying and fluidised bed granulation processes.

Especially suitable are spray-drying processes in which the active ingredient solution is sprayed into a chamber with circulating hot air. The atomisation of the solution is effected e.g. using unitary or binary nozzles or is brought about by the spinning effect of a rapidly rotating disc. In order to increase the particle size, the spray-drying process may be combined with an additional agglomeration of the liquid particles with solid nuclei in a fluidised bed that forms an integral part of the chamber (so-called fluid spray). The fine particles (<100 μm) obtained by a conventional spray-drying process may, if necessary after being separated from the exhaust gas flow, be fed as nuclei, without further treatment, directly into the atomizing cone of the atomiser of the spray- Preference is given to compounds of formula (2b), (2c) or (2d) wherein $R_1, R_2, R_3, R_4$ signifies H, OH, —$NR_{15}R_{16}$, —$N^{\oplus}R_{15}R_{16}R_{17}$, or $C_1$-$C_{18}$alkyl, $R_5$ denotes H, $R_6$ denotes H, OH, $C_1$-$C_4$alkyl or phenyl;

$R_7, R_8, R_9, R_{10}$ are each independently of the other hydrogen, OH, unsubstituted or substituted $C_1$-$C_8$alkyl, unsubstituted or substituted phenyl, —$NR_{15}R_{16}$; —$N^{\oplus}R_{15}R_{16}R_{17}$;

$R_{15}, R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms;

$R_{14}$ is hydrogen or $C_1$-$C_4$alkyl or phenyl;

$R_{18}, R_{19}$ and $R_{20}$ are independently of each other hydrogen, $C_1$-$C_{18}$alkyl, phenyl, cyano; halogen, nitro, —OH; —$COOR_{13}$ or —$SO_3R_{13}$ wherein $R_{13}$ is hydrogen or an alkali metal cation;

—$SR_{14}$, —$SO_2R_{14}$ or —$OR_{14}$ wherein $R_{14}$ hydrogen or $C_1$-$C_4$alkyl.

A further aspect of the invention is a metal complex of formula (1)

$$[L_n Me_m X_p]^z Y_q \quad (1),$$

wherein

Me is manganese, titanium, iron, cobalt, nickel or copper,

X is a coordinating or bridging radical, n and m are each independently of the other an integer having a value of from 1 to 8, p is an integer having a value of from 0 to 32, z is the charge of the metal complex, Y is a counter-ion, q=z/(charge of Y), and L is a ligand of formula (2b), (2c) or (2d) as described above.

All preferences as mentioned above (for the use) apply also for the metal complex as such.

Another aspect of the present invention is a process of production of compounds of formula (2b), (2c) and (2d). A suitable process is for example outlined in the following reaction scheme.

wherein all the substituents have the meanings as defined above.

The starting materials are known or can be prepared according to standard processes.

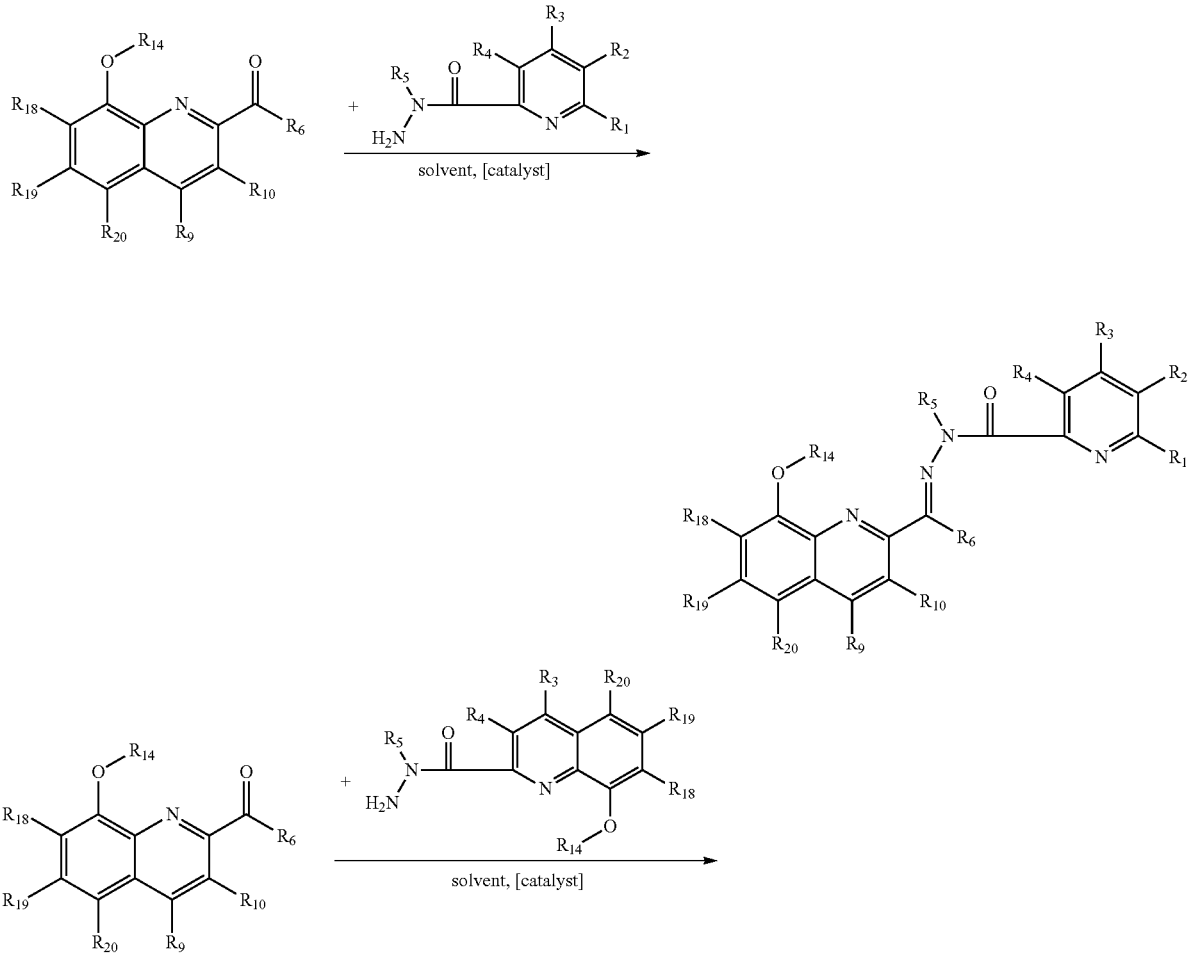

-continued

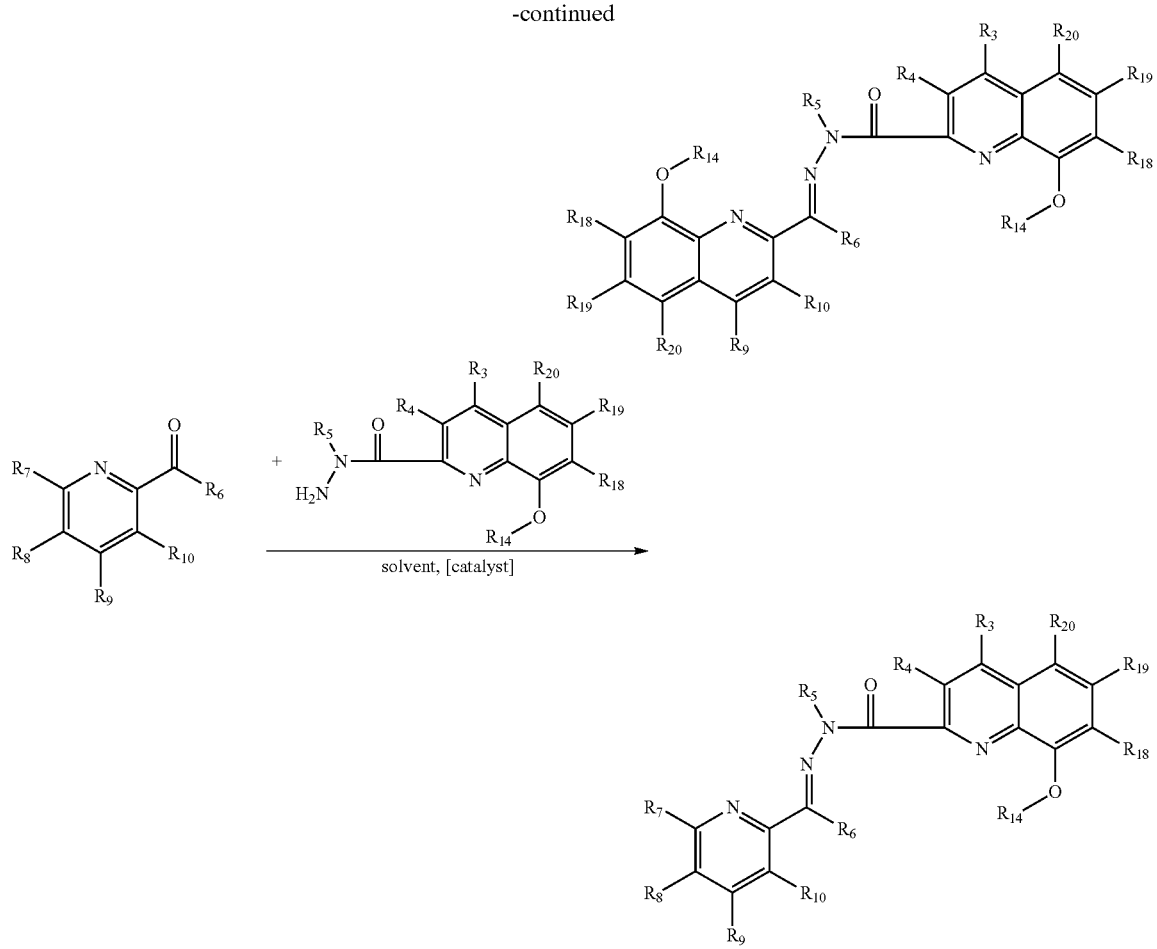

The reactions are preferably carried out with no solvent or in an organic solvent and more preferably in an alcohol solvent, such as methanol, ethanol, t-butanol, n-octanol-(1), and ethylene glycol; an aromatic solvent such as toluene, xylene, mesitylene and benzene; a hydrocarbon solvent such as heptane, and petroleum ether, an ester solvent such as ethyl acetate, and methyl acetate; an amide solvent such as dimethylformamide, dimethylacetamide, diethylacetamide, diethylpropionamide, and 1-methylpyrrolidone; an ether solvent such as diethyl ether, dioxane, and tetrahydrofuran; and a polar solvent such as dimethylsulfoxide. Most preferably, the solvent is any of water, methanol, ethanol, 1-propanol and 2-propanol.

The reaction temperature may be between −78° C. and the boiling point of the solvent used, but is preferably between 0° C. and 100° C., and more preferably between 10° C. and 60° C.

The molar ratio of the hydrazide may be from 0.1 to 100 times, and preferably from 0.5 to 10 times, and more preferably from 0.8 to 1.2 times depending on the carbonyl derivative.

Advantageously a catalyst is used. Preferred catalysts are Lewis acids. More preferably used are Bronsted acids. The acids may be organic or inorganic, a Lewis acid or a Bronsted acid.

Examples for an organic acid are carboxylic acids, such as formic acid, acetic acid, propionic acid and others. Amino acids are also suitable like leucine, alanine or proline. Preferably sulfonic acids are used, such as methane sulfonic acid, p-toluenesulfonic acid, benzene sulfonic acid, trifluoromethane sulfonic acid. Also the so-called superacids can be used, such as mixtures of sulphuric acid with $SO_3$, $FSO_3H$, $ClSO_3H$, $H[B(OSO_3H)_4]$ or $HSbF_6$. Most preferred are hydrogen halides like HCl or HBr.

The reaction is also possible in the presence of a Lewis acid. Examples of a Lewis acid are borotrifluoride, the bromides of phosphorus and aluminium and first of all the chlorides of boron, aluminium, phosphorus, antimony, arsenic, iron, zinc and tin. In the $5^{th}$ edition of March's Advanced Organic Chemistry (John Wiley & Sons, Inc.) in chapter 8 acids are described which can catalyze these condensation reactions.

The amount (mass) of the solvent is from 0.5 to 50 times, and preferably from 1 to 10 times, and more preferably from 1 to 5 times as much as the mass of the reactants.

The reaction end point may be confirmed, for example, through thin layer chromatography, gas chromatography or high performance liquid chromatography. After the reaction, the product may be obtained from the reaction mixture through ordinary product isolation by, for example, filtration, liquid-liquid separation, column chromatography, or crystallization by addition of a poor solvent to the reaction mixture, or by distillation.

Compounds in which $R_6$ is a hydroxyl group can be prepared according to the following reaction scheme:

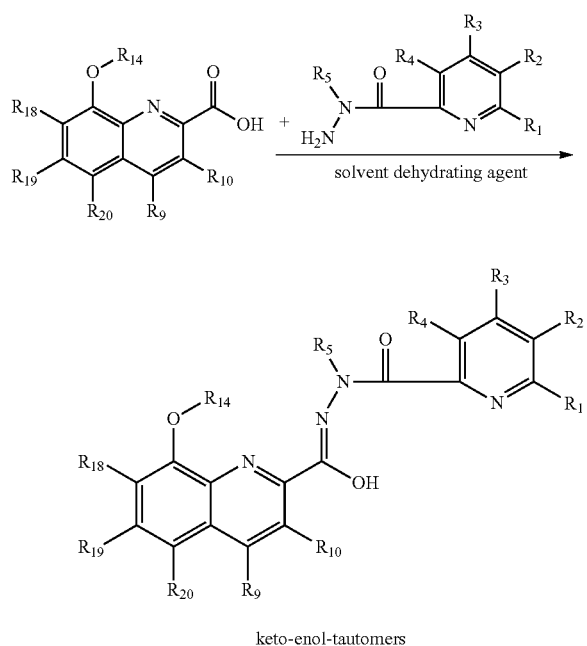

keto-enol-tautomers

Preferences and conditions mentioned above apply also for this reaction.

The molar ratio of the hydrazide to the carboxylic acid derivative may be from 0.1 to 100 times, preferably from 0.5 to 10 times and more preferably from 0.8 to 1.2.

Advantageously water is removed during the course of the reaction by use of a dehydrating agent, silica gel, or a molecular sieve. Examples of dehydrating agents are N,N'-dicyclohexylcarbodiimid (DCC) and N,N'-carbonyldiimidazole. In the 5$^{th}$ edition of March's Advanced Organic Chemistry (John Wiley & Sons, Inc.) in the chapter 10-23 (Esterification of Carboxylic Acids) such dehydrating agents are described which can catalyze these condensation reactions.

The metal complexes of formula (1) are produced according to common processes. A suitable way is to react the ligands of formula (2) with a suitable metal salt at a desired molar ratio.

Particularly suitable individual ligands are summarized in Table A

TABLE A

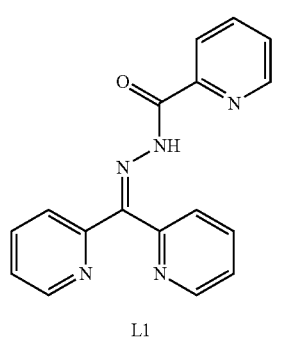

L1

TABLE A-continued

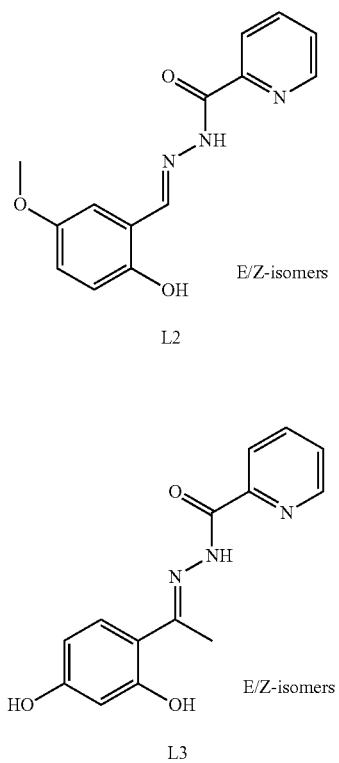

L2

L3

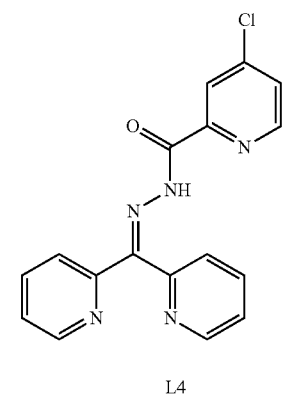

L4

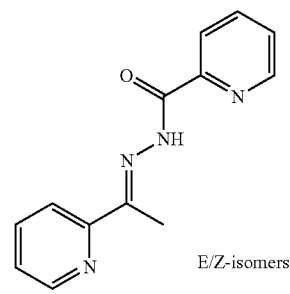

L5

TABLE A-continued
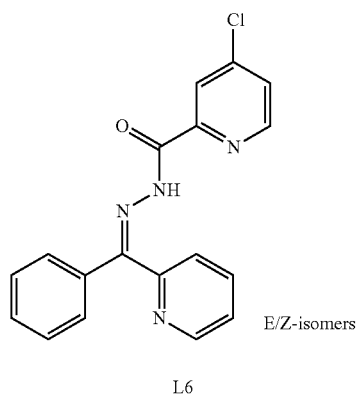
E/Z-isomers
L6
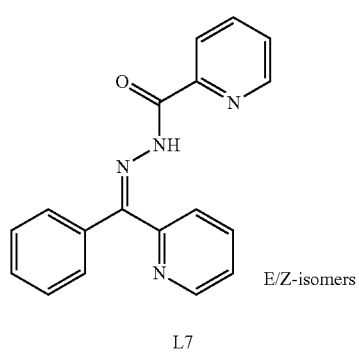
E/Z-isomers
L7
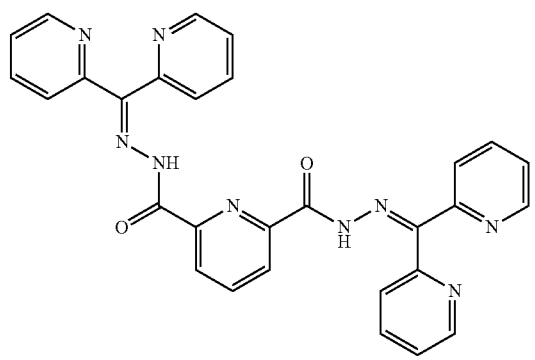
L8
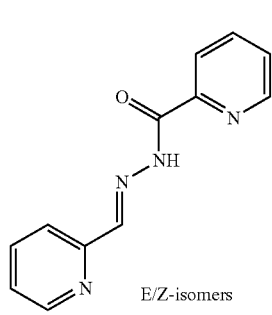
E/Z-isomers
L9
TABLE A-continued
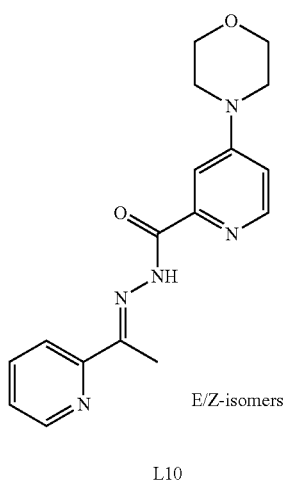
E/Z-isomers
L10
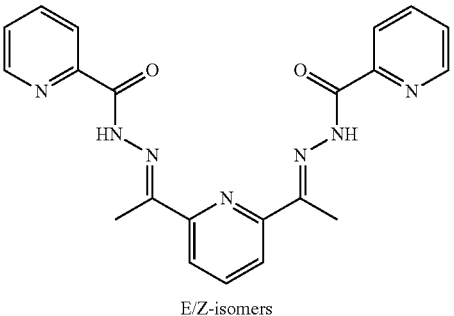
L11
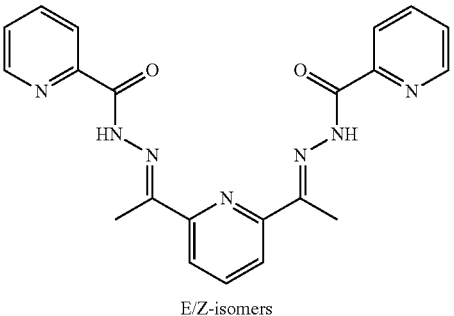
E/Z-isomers
L12

TABLE A-continued
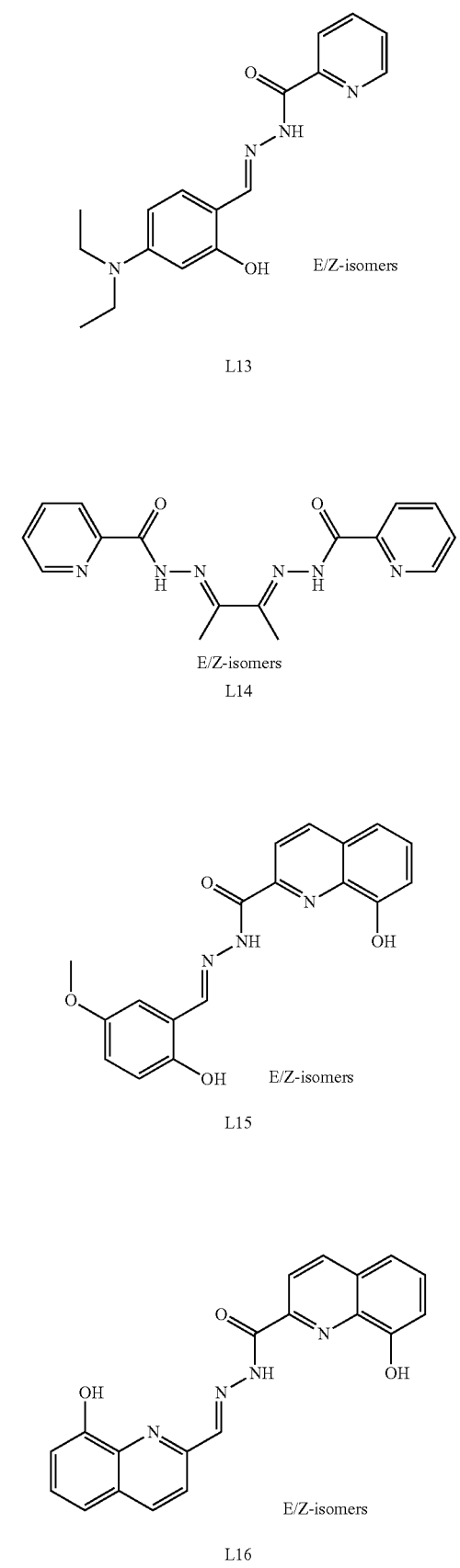
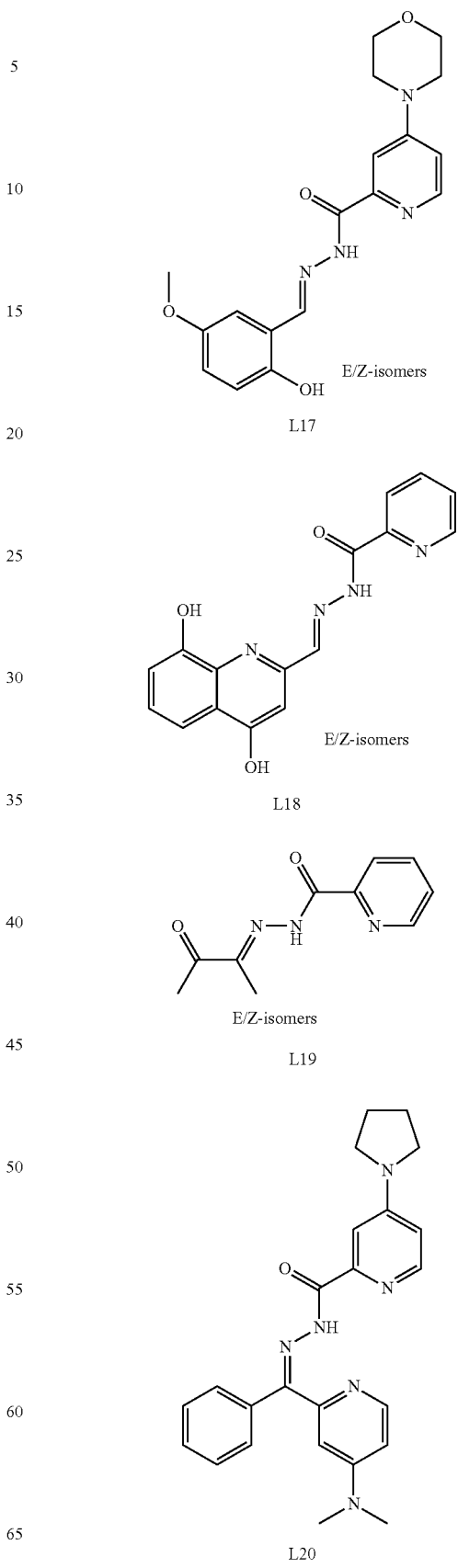

TABLE A-continued
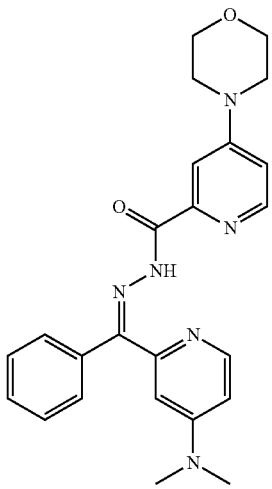
L21
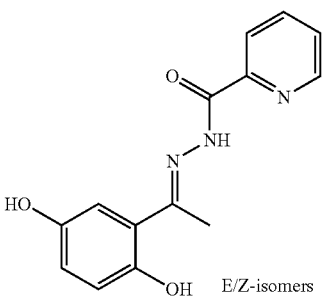
E/Z-isomers
L22
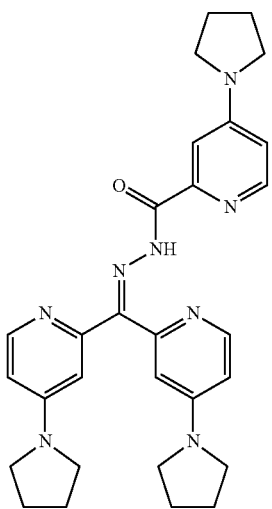
L23
TABLE A-continued
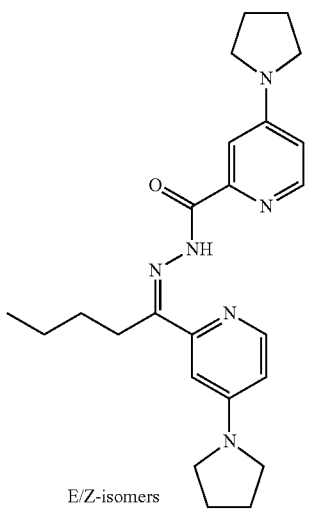
E/Z-isomers
L24
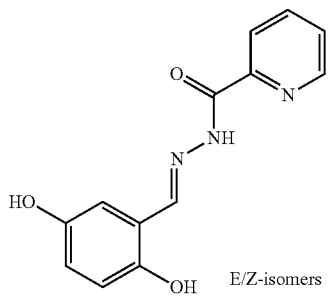
E/Z-isomers
L25
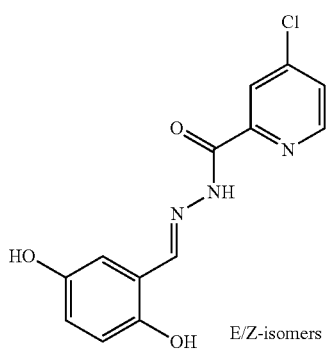
E/Z-isomers
L26

TABLE A-continued
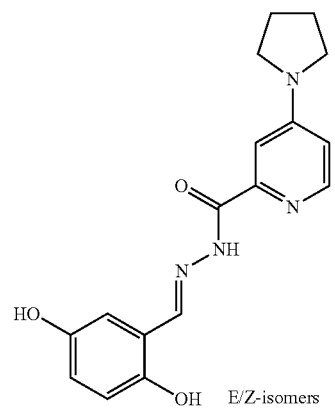
L27 E/Z-isomers
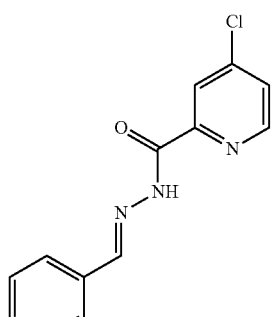
L28 E/Z-isomers
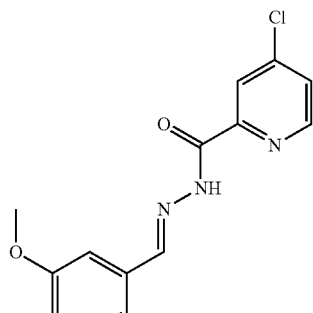
L29 E/Z-isomers
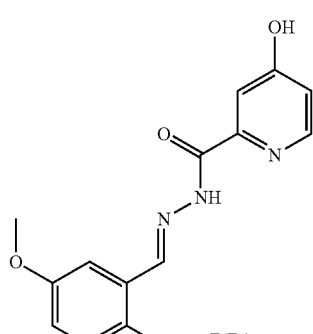
L30 E/Z-isomers
TABLE A-continued
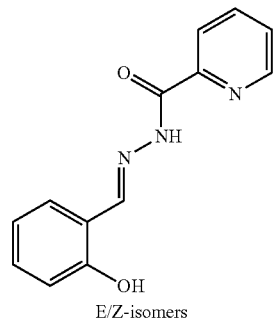
L31 E/Z-isomers
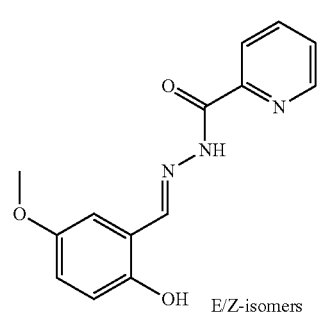
L32 E/Z-isomers
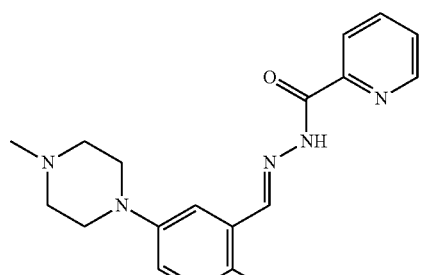
L33 E/Z-isomers
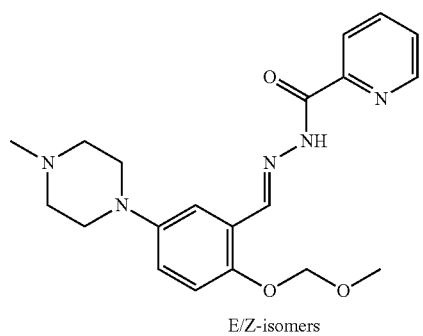
L34 E/Z-isomers TABLE A-continued
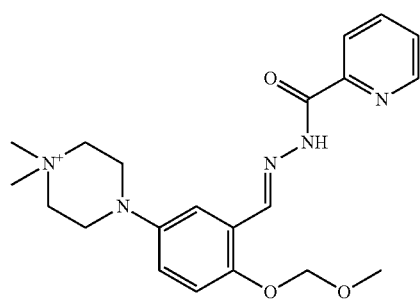
E/Z-isomers
L35
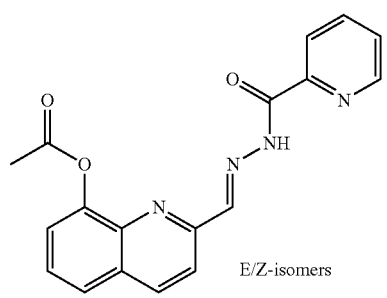
E/Z-isomers
L36
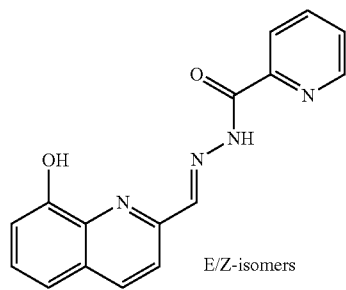
E/Z-isomers
L37
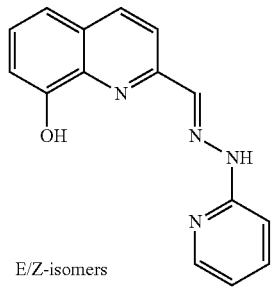
E/Z-isomers
L38
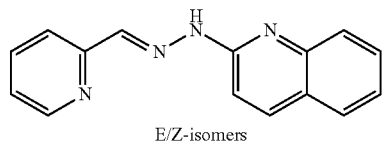
E/Z-isomers
L39
TABLE A-continued
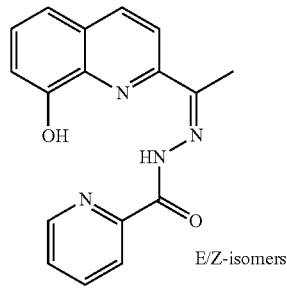
E/Z-isomers
L40
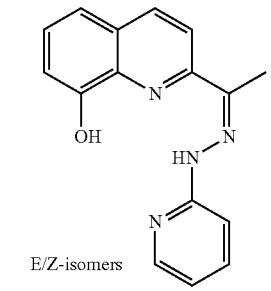
E/Z-isomers
L41
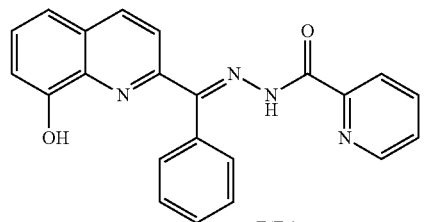
E/Z-isomers
L42
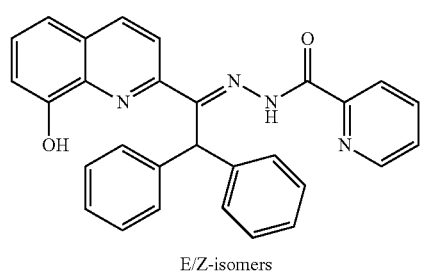
E/Z-isomers
L43
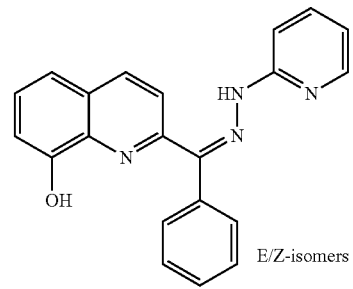
E/Z-isomers
L44

TABLE A-continued

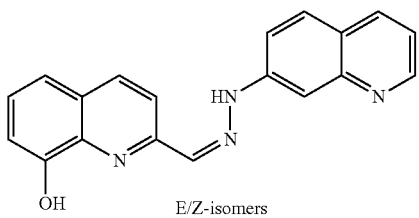

E/Z-isomers

L45

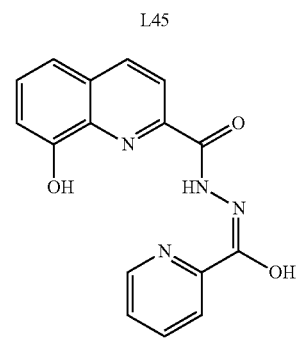

keto-enol-tautomers

L46

The following Examples serve to illustrate the invention.
Parts and percentages relate to weight, unless otherwise indicated. Temperatures are in degrees Celsius, unless otherwise indicated.

EXAMPLES

Synthesis Example A1

Preparation of

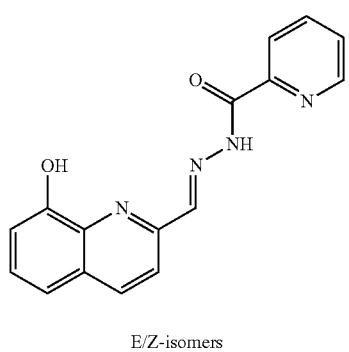

E/Z-isomers (compound 101, L37)

A mixture of 0.28 g of 2-picolinyl hydrazide in 8 mL of ethanol is heated to 40° C. and stirred for 15 minutes at this temperature. A hot solution of 0.35 g of 8-hydroxyquinoline-2-carboxaldehyde in 4 mL of ethanol is added in portion. Finally 0.25 mL of concentrated hydrochloric acid is added. The reaction mixture is stirred for 1 hour at 40° C. before an orange powder is filtrated off and washed with water. After column chromatography (silica gel) using toluene/methanol (9:1) as eluent the product is isolated yielding 0.11 g of a beige powder.

$^1$H NMR ([D$_6$]DMSO): δ=16.15 (s, 1H), 9.66 (s, 1H), 8.84 (d, 1H), 8.63 (d, 1H), 8.29 (d, 1H), 8.19 (t, 1H), 7.96 (s, 1H), 7.93 (d, 1H), 7.80-7.84 (m, 1H), 7.64 (t, 1H), 7.55 (d, 1H), 7.35 (d, 1H).

Synthesis Example A2

Preparation of

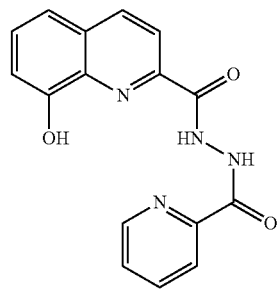

keto-enol-tautomers (compound 102, L46)

0.45 g of N,N'-carbonyldiimidazole and 0.54 g of 8-hydroxyquinoline2-carboxylic acid are mixed together in 2 mL of THF. The mixture is stirred for 1 hour at room temperature. A mixture of 0.31 g of 2-picolinyl hydrazid in 1 mL of THF is added under cooling with cold water. The mixture is then warmed slowly to room temperature and stirred for 16 hours. After removal of ethanol by distillation the residue is taken up in acetone and re-precipitated on addition of water. The product is filtrated off and dried at high vacuum at 80° C. for 4 hours yielding 0.86 g of a pale beige powder. $^1$H-NMR ([D$_6$]DMSO): δ=11.42 (s, 1H), 10.85 (s, 1H), 10.21 (s, 1H), 8.75 (d, 1H), 8.56 (d, 1H), 8.16 (d, 1H), 8.04-8.12 (m, 2H), 7.70 (t, 1H), 7.62 (t, 1H), 7.52 (d, 1H), 7.21 (d, 1H).

Synthesis Example A3

Preparation of (compound 103

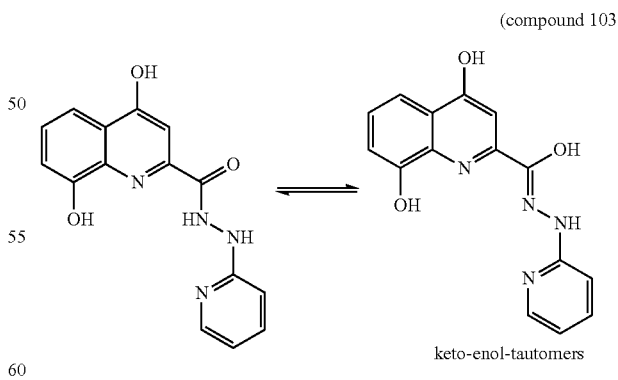

keto-enol-tautomers 0.30 g of xanthurenic acid is added to a mixture of 0.23 g of N,N'-carbonyldiimidazole in 2 mL of tetrahydrofurane (THF). The suspension is stirred of 2 hours at room temperature. 0.14 g of 2-hydrazino pyridine dissolved in 2 mL of THF are added dropwise under cooling with cold water. The resulting suspension is stirred for 20 hours at room temperature.

After addition of mL of water the yellow suspension is stirred for another hour. The product is then filtered off, washed with water and dried in high vacuum at 80° C. yielding 0.18 g of a dark-yellow powder. $^1$H NMR ([D$_6$]DMSO): δ=11.25 (s, 1H), 9.93 (s, 1H), 8.53 (s, 1H), 8.05 (d, 1H), 7.40-7.59 (m, 4H), 7.11 (d, 1H), 6.72 (t, 1H), 6.65 (d, 1H).

Synthesis Example A4

Preparation of

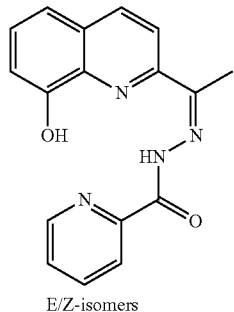

E/Z-isomers (compound 104, L40)

0.11 g of 2-picolinylhydrazide is dissolved in 2 mL of 1-butanol. The mixture is heated up to 50° C. under stirring before a mixture of 0.15 g of 2-acetyl-8-hydroxy-quinoline (prepared according to a synthesis protocol as described in patent application WO 2004/007461) in 2 mL of 1-butanol is added dropwise. After stirring the reaction mixture for 20 minutes at 50° C. 2 drops of concentrated hydrochloric acid is added. After stirring the reaction mixture for another 2 hours at 50° C. the product is filtered off, washed with 2-butanol, saturated NaHCO$_3$ solution and finally with methanol. After drying in vacuum, 0.07 g of the product is obtained as yellowish red powder.

UV (MeOH): λ$_{max}$=292 nm, melting point=200° C.

Synthesis Example 5

Preparation of

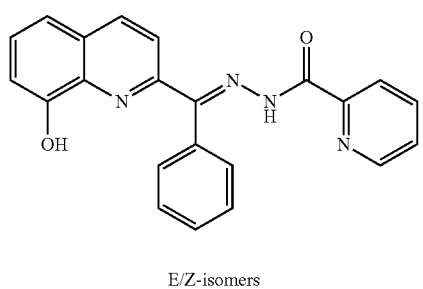

E/Z-isomers (compound 105, L42)

A hot solution of 0.2 g of (8-hydroxy-quinolin-2-yl)-phenyl-methanone (prepared according to the synthesis protocol of 2-acetyl-8-hydroxy-quinoline as described in patent application WO 2004/007461; instead of methyl magnesiumbromide the reagent phenyl magnesiumchloride is used) in 6 mL of ethanol is added to a mixture of 0.11 g of 2-picolinyl hydrazide in 2 mL of ethanol at a temperature of 80° C. To the resulting yellow reaction mixture 1 drop of concentrated hydrochloric acid is given. After stirring the reaction mixture at 80° C. for 2 hours a saturated NaHCO$_3$ solution is added. The product is then filtered off, washed with water and dried in vacuum at 80° C. yielding 0.18 g of a dark yellow powder.

UV (MeOH): λ$_{max}$=261 nm; melting point=229-239° C.

Synthesis Example A6

Preparation of

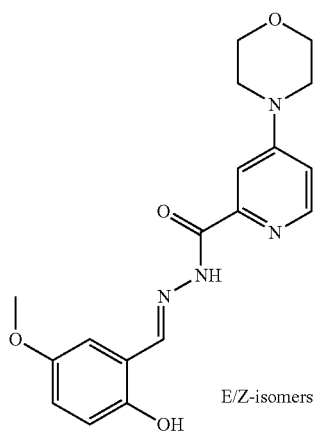

E/Z-isomers (compound 106, L17)

According to a literature procedure described in J. Chem. Soc., Dalton Trans. (2008) on pages 1706-1710 a mixture of 0.97 g of 2-hydroxy-5-methoxy-benzaldehyde in 6 mL of ethanol is added dropwise to a mixture of 1.41 g of 4-morpholin-4-yl-pyridine-2-carboxylic acid hydrazide in 25 mL of ethanol. Finally 0.5 mL of concentrated hydrochloric acid is added. The reaction mixture is stirred over night at room temperature before a yellow precipitate is filtrated off and washed twice with 20 mL of ethanol. After drying in vacuum at 80° C. the product is isolated yielding 2.08 g of a beige powder.

$^1$H NMR ([D$_6$]DMSO): δ=13.68 (s, 1.3H), 10.50 (s, 1H), 9.10 (s, 1H), 8.36 (s, 1H), 8.25 (d, 1H), 7.26 (d, 1H), 7.13 (s, 1H), 6.97-6.92 (m, 2H), 3.84 (s, 4H), 3.77 (s, 4H), 3.74 (s, 3H).

The starting material 4-morpholin-4-yl-pyridine-2-carboxylic acid hydrazide is synthesized according to a procedure described in J. Org. Chem. (Vol. 64, No. 13, 1999) on page 4659. Hereby a mixture of 1.75 g of 4-chloro-pyridine-2-carboxylic acid hydrazide and 8.80 g of morpholine is heated for 14 hours at 90° C. After cooling to room temperature 20 mL of ethanol are added. A colorless precipitate is filtered off and discarded. The filtrate is kept over night from which the product precipitates. The product is filtered off and dried at vacuum yielding 0.39 g of a beige powder. $^1$H NMR ([D$_6$]DMSO): δ=9.05 (s, 1H), 8.21 (d, 1H), 7.58 (d, 1H), 6.72 (dd, 1H), 3.84 (m, 4H), 3.38 (m, 4H).

Synthesis Example A7

Preparation of

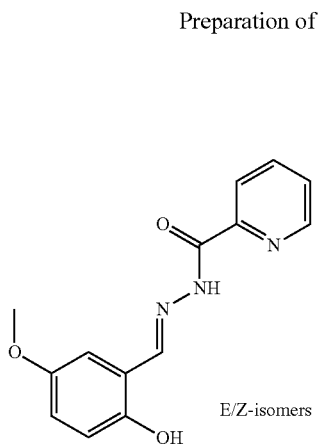

E/Z-isomers (compound 107, L2)

According to a literature procedure described in J. Chem. Soc., Dalton Trans. (2008) on pages 1706-1710 a mixture of 0.97 g of 2-hydroxy-5-methoxy-benzaldehyde in 6 mL of ethanol is added dropwise to a mixture of 1.41 g of 2-picolinyl hydrazide in 25 mL of ethanol. Finally 0.5 mL of concentrated hydrochloric acid is added. The reaction mixture is refluxed for 2 hours before a precipitate is filtered off, dried in vacuum at 80° C. yielding 1.41 g of the desired product. Melting point: 159-167° C.

Synthesis Example A8

Preparation of

E/Z-isomers (compound 108, L5)

According to a literature procedure described in J. Chem. Soc., Dalton Trans. (2008) on pages 1706-1710 a mixture of 0.77 g of 2-acetylpyridine in 6 mL of ethanol is added dropwise to a mixture of 0.87 g of 2-picolinyl hydrazide in 25 mL of ethanol. Finally 0.5 mL of concentrated hydrochloric acid is added. The reaction mixture is refluxed for 2 hours before the desired product is filtered off, dried in vacuum at 80° C. yielding 1.36 g of a yellow powder. Melting point: 186-191° C.

Synthesis Example A9

Preparation of

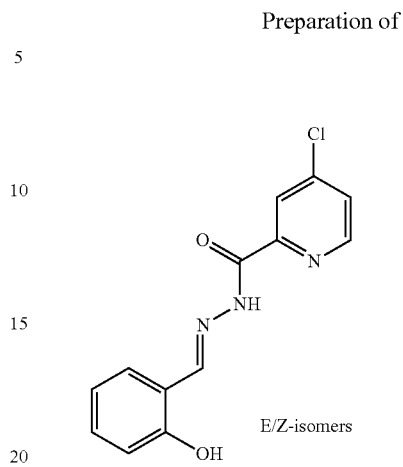

E/Z-isomers (compound 109, L28)

According to a literature procedure described in J. Chem. Soc., Dalton Trans. (2008) on pages 1706-1710 a mixture of 0.6 g of 4-chloro-pyridine-2-carboxylic acid hydrazide in 15 mL of ethanol is stirred for 15 minutes at 40° C. A mixture of 0.39 g of 2-hydroxy-benzaldehyde in 5 mL of ethanol is added dropwise. Finally 0.5 mL of concentrated hydrochloric acid is added. The reaction mixture is stirred at room temperature for 3 days before the desired product is filtered off, washed with water, dried in vacuum at 70° C. yielding 0.61 g of a colorless powder. $^{13}$C NMR ([D$_6$]DMSO): δ=159.27, 157.59, 150.89, 150.44, 150.10, 144.65, 131.55, 129.77, 126.94, 122.73, 119.30, 118.50, 116.42.

Synthesis Example A10

Preparation of

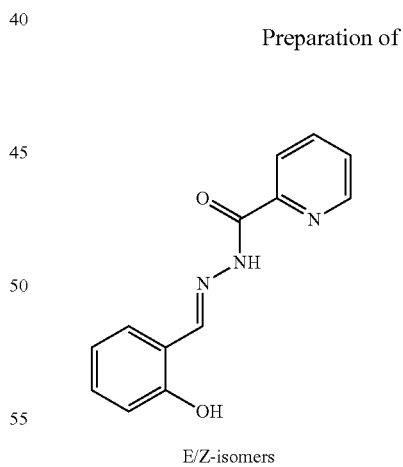

E/Z-isomers (compound 110, L31)

According to a literature procedure described in J. Chem. Soc., Dalton Trans. (2008) on pages 1706-1710 a mixture of 0.43 g of 2-picolinyl hydrazide in 15 mL of ethanol is stirred for 15 minutes at 40° C. A mixture of 0.39 g of 2-hydroxy-benzaldehyde in 5 mL of ethanol is added dropwise. Finally 0.25 mL of concentrated hydrochloric acid is added. The reaction mixture is stirred at room temperature before the desired product is filtered off, washed with water, dried in vacuum at 70° C. yielding 0.60 g of a colorless powder. $^1$H NMR ([D$_6$]DMSO): δ=12.52 (s, 1H), 11.43 (s, 1H), 8.86 (s, 1H), 8.74 (d, 1H), 8.15 (m, 1H), 8.08 (m, 1H), 7.70 (s, 1H), 7.48 (d, 1H), 7.34 (m, 1H), 6.97-6.92 (m, 2H).

APPLICATION EXAMPLES

Application Example B1

Peroxide Bleaching of Morin in Solution

10 μM catalyst solution (1:1 complex of Mn(II) chloride tetrahydrate with the ligand given in Table 1 in water or methanol) are added at time t=0 to a solution of 160 μM morin in 10 mM carbonate buffer, pH 10 containing 10 mmol/l hydrogen peroxide. The solution is located in a thermostatically controllable vessel, equipped with a magnetic stirrer, at 23° C. The extinction of the solution is measured at 410 nm over a period of 10 min. The values for the decoloration after 5 min. are indicated as percentages:

TABLE 1

| Ligand | Extent of the decoloration after 5 min (%) |
|---|---|
| L2 | 86 |
| L17 | 55 |
| L28 | 50 |
| L31 | 85 |
| L37 | 90 |
| L42 | 78 |
| Reference without catalyst | 13 |

The bleaching action in the presence of the compounds according to the invention is superior to the reference sample of 10 mM hydrogen peroxide alone.

Application Example 2

Peroxide Bleaching Action in Washing Agents 7.5 g of white cotton fabric and 2.5 g of tea-stained cotton fabric are treated in 80 ml of washing liquor. The liquor contains a standard washing agent (ECE, 456 IEC) in a concentration of 7.5 g/l. The hydrogen peroxide concentration is 8.6 mmol/l. The catalyst concentration (1:1 complex of manganese(II) chloride tetrahydrate with the ligand given in Table 2, prepared in methanolic solution with the addition of a small amount of lithium hydroxide) is 50 μmol/l. The washing process is carried out in a steel beaker in a LINITEST apparatus for 30 minutes at 40° C. For evaluating the bleaching results, the increase in the lightness DY (difference in lightness according to CIE) of the stains brought about by the treatment is determined spectrophotometrically in comparison with values obtained without the addition of catalyst.

TABLE 2

| 1:1 Mn complex with ligand | DY increase |
|---|---|
| L2 | 3.4 |
| L5 | 2.7 |
| L17 | 2 |
| L28 | 3.5 |
| L31 | 2 |
| L40 | 2.3 |
| L42 | 6 |

The manganese complexes exhibit a very good bleaching action.

The invention claimed is:
1. A detergent, cleaning, disinfecting or bleaching composition comprising
I) from 1 to 50 wt-%, based on the total weight of the composition, A) of at least one anionic surfactant and/or B) of a non-ionic surfactant,
II) from 0 to 70 wt-%, based on the total weight of the composition, C) of at least one builder substance,
III) 1-99 wt-%, based on the total weight of the composition, D) of at least one peroxide and/or one peroxide-forming substance, O$_2$ and/or air,
IV) E) 0.005 to 2 wt-% of at least one metal complex compound of formula (1),
V) 0-20 wt-%, based on the total weight of the composition, of at least one further additive, and
VI) water ad 100 wt-%, based on the total weight of the composition,

$$[L_nMe_mX_p]^zY_q \quad (1)$$

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y), and
L is a ligand of formula (2)

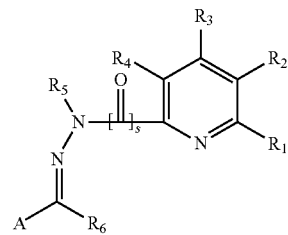

wherein
s=0 or 1;
A denotes

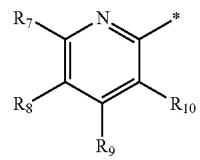

or

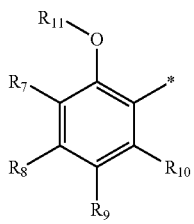

or

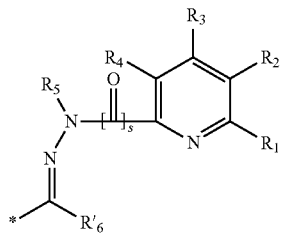

or

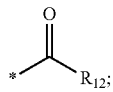

$R_6$ denotes A or hydrogen, $C_1$-$C_{28}$ alkyl, $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl or heteroaryl, or OH;

$R'_6$ denotes hydrogen, $C_1$-$C_{28}$ alkyl, $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl or heteroaryl, or OH;

* signifies the bond/linkage to the structure of formula (2);

$R_1$ denotes

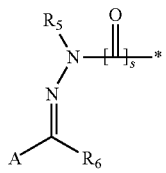

or hydrogen, $C_1$-$C_{28}$ alkyl, $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, cyano, halogen, nitro, or unsubstituted or substituted aryl, or unsubstituted or substituted heteroaryl, —$COOR_{13}$ or —$SO_3R_{13}$ wherein $R_{13}$ is in each case hydrogen, a cation or unsubstituted or substituted $C_1$-$C_{18}$alkyl or unsubstituted or substituted aryl;

or $R_1$ is —$SR_{14}$, —$SO_2R_{14}$ or —$OR_{14}$ wherein
$R_{14}$ is in each case hydrogen or unsubstituted or substituted $C_1$-$C_{18}$alkyl or unsubstituted or substituted aryl;

or $R_1$ is —$NR_{15}R_{16}$, —($C_1$-$C_6$alkylene)-$NR_{15}R_{16}$, —$N^{\oplus}R_{15}R_{16}R_{17}$, —($C_1$-$C_6$alkylene)-$N^{\oplus}R_{15}R_{16}R_{17}$, —$N(R_{14})$—($C_1$-$C_6$alkylene)-$NR_{15}R_{16}$, —$N[(C_1$-$C_6$alkylene)-$NR_{15}R_{16}]_2$, —$N(R_{14})$—($C_1$-$C_6$alkylene)-$N^{\oplus}R_{15}R_{16}R_{17}$, —$N[(C_1$-$C_6$alkylene)-$N^{\oplus}(R_{15}R_{16}R_{17})]_2$, —$N(R_{14})$—N—$R_{15}R_{16}$ or $^{\oplus}$—$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms, $R_7$ denotes

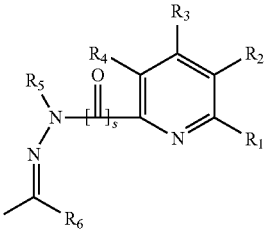

or hydrogen; $C_1$-$C_{28}$ alkyl; $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, cyano, halogen, nitro, —$COOR_{13}$ or —$SO_3R_{13}$ wherein $R_{13}$ is in each case hydrogen, a cation or unsubstituted or substituted $C_1$-$C_{18}$alkyl or unsubstituted or substituted aryl;

or $R_7$ is —$SR_{14}$, —$SO_2R_{14}$ or —$OR_{14}$ wherein
$R_{14}$ is in each case hydrogen or unsubstituted or substituted $C_1$-$C_{18}$alkyl or unsubstituted or substituted aryl;

or $R_7$ is —$NR_{15}R_{16}$, —($C_1$-$C_6$alkylene)-$NR_{15}R_{16}$, —$N^{\oplus}R_{15}R_{16}R_{17}$, —($C_1$-$C_6$alkylene)-$N^{\oplus}R_{15}R_{16}R_{17}$, —$N(R_{14})$—($C_1$-$C_6$alkylene)-$NR_{15}R_{16}$, —$N[(C_1$-$C_6$alkylene)-$NR_{15}R_{16}]_2$, —$N(R_{14})$—($C_1$-$C_6$alkylene)-$N^{\oplus}R_{15}R_{16}R_{17}$, —$N[(C_1$-$C_6$alkylene)-$N^{\oplus}R_{15}R_{16}R_{17}]_2$, —$N(R_{14})$—N—$R_{15}R_{16}$ or —$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms;

* signifies the bond/linkage to A;

$R_2$, $R_3$, $R_4$, $R_8$, $R_9$, $R_{10}$, $R_{18}$, $R_{19}$, $R_{20}$, $R_{21}$, $R_{22}$, $R_{23}$, $R_{24}$, $R_{25}$, $R_{26}$, and $R_{27}$ are each independently of the others hydrogen, unsubstituted or substituted $C_1$-$C_{18}$alkyl, $C_2$-$C_{28}$alkenyl, $C_3$-$C_{12}$cycloalkyl, $C_3$-$C_{12}$cycloalkenyl or unsubstituted or substituted aryl or unsubstituted or substituted heteroaryl, cyano, halogen, nitro, —OH, —$COOR_{13}$ or —$SO_3R_{13}$ wherein $R_{13}$ is in each case hydrogen, a cation or unsubstituted or substituted $C_1$-$C_{18}$alkyl or unsubstituted aryl;

or are —$SR_{14}$, —$SO_2R_{14}$ or —$OR_{14}$ wherein
- $R_{14}$ is in each case hydrogen or unsubstituted or substituted $C_1$-$C_{18}$alkyl or unsubstituted or substituted aryl;
- or are —$NR_{15}R_{16}$, —($C_1$-$C_6$alkylene)-$NR_{15}R_{16}$, —$N^{\oplus}R_{15}R_{16}R_{17}$, —($C_1$-$C_6$alkylene)-$N^{\oplus}R_{15}R_{16}R_{17}$, —$N(R_{14})$—($C_1$-$C_6$alkylene)-$NR_{15}R_{16}$, —$N[(C_1$-$C_6$alkylene)-$NR_{15}R_{16}]_2$, —$N(R_{14})$—($C_1$-$C_6$alkylene)-$N^{\oplus}R_{15}R_{16}R_{17}$, —$N[(C_1$-$C_6$alkylene)-$N^{\oplus}R_{15}R_{16}R_{17}]_2$, —$N(R_{14})$—N—$R_{15}R_{16}$ or —$N(R_{14})$—$N^{\oplus}R_{15}R_{16}R_{17}$, wherein
- $R_{14}$ is as defined above and
- $R_{15}$, $R_{16}$ and $R_{17}$ are each independently of the other(s) hydrogen or unsubstituted or substituted $C_1$-$C_{18}$alkyl or unsubstituted or substituted aryl, or
- $R_{15}$ and $R_{16}$, together with the nitrogen atom linking them, form an unsubstituted or substituted 5-, 6- or 7-membered ring which may contain further hetero atoms and
- $R_5$, $R_{11}$ and $R_{12}$ denote independently of each other hydrogen, $C_1$-$C_{28}$ alkyl, $C_2$-$C_{28}$ alkenyl, $C_2$-$C_{22}$ alkinyl, $C_3$-$C_{12}$ cycloalkyl, $C_3$-$C_{12}$ cycloalkenyl, $C_7$-$C_{28}$ aralkyl, $C_1$-$C_{20}$ heteroalkyl, $C_3$-$C_{12}$ cycloheteroalkyl, $C_5$-$C_{16}$ heteroaralkyl, unsubstituted or substituted aryl, or unsubstituted or substituted heteroaryl;

or $R^1$ and $R^2$, and/or $R^7$ and $R^8$ are a group

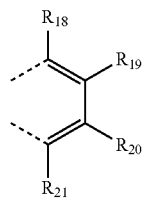

or

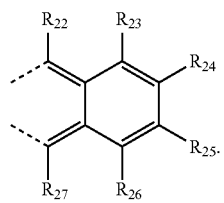

A denotes

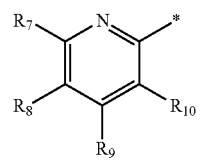

or

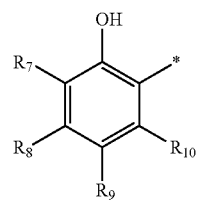

or

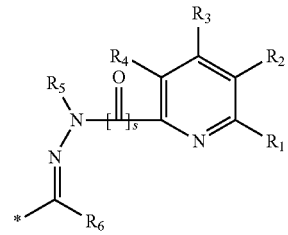

or

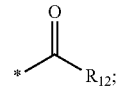

$R_7$, $R_8$, $R_9$, $R_{10}$ and $R_{12}$ are each independently of the other hydrogen, OH, unsubstituted or substituted $C_1$-$C_{18}$alkyl, unsubstituted or substituted aryl, —$NR_{15}R_{16}$ or —$N^{\oplus}R_{15}R_{16}R_{17}$ and $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

2. A composition according to claim 1 wherein
X is $CH_3CN$, $H_2O$, $F^-$, $Br^-$, $H^-$, $O_2^{2-}$, $O^{2-}$, $R_{101}COO^-$, $R_{101}O^-$, $LMeO^-$ or $LMeOO^-$, wherein $R_{101}$ is hydrogen, unsubstituted or substituted $C_1$-$C_{18}$alkyl or phenyl; and
Y is $R_{102}COO^-$, $ClO_4^-$, $BF_4^-$, $PF_6^-$, $R_{102}SO_3^-$, $R_{102}SO_4^-$, $SO_4^{2-}$, $NO_3^-$, $F^-$, $Cl^-$, $Br^-$ or $I^-$ where $R_{102}$ is hydrogen or unsubstituted or substituted $C_1$-$C_{18}$alkyl or unsubstituted or substituted aryl.

3. A composition according to claim 1 wherein in formula (2) $R_1$, $R_2$, $R_3$, $R_4$ independently signify H, OH, —$NR_{15}R_{16}$, —$N^{\oplus}R_{15}R_{16}R_{17}$, or $C_1$-$C_{18}$alkyl,
s is 1,
$R_5$ denotes H,
$R_6$ denotes H, OH, A, $C_1$-$C_{18}$alkyl, unsubstituted or substituted phenyl;

4. A composition according to claim 1 wherein in formula (2) $R_1$, $R_2$, $R_3$, $R_4$ independently signify H, OH, —$NR_{15}R_{16}$, —$N^{\oplus}R_{15}R_{16}R_{17}$ or $C_1$-$C_{18}$alkyl,
s is 1,
$R_5$ denotes H,
$R_6$ denotes H, methyl or OH, A denotes

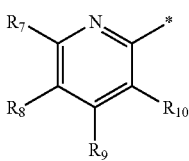

or

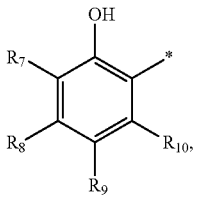

$R_7$, $R_8$, $R_9$, $R_{10}$ are each independently of the other hydrogen, OH, unsubstituted or substituted $C_1$-$C_{18}$alkyl, unsubstituted or substituted phenyl, —$NR_{15}R_{16}$ or —$N^{\oplus}R_{15}R_{16}R_{17}$ and $R_{15}$, $R_{16}$ and $R_{17}$ are each independently of the other(s) hydrogen or unsubstituted or substituted $C_1$-$C_{18}$alkyl or unsubstituted or substituted aryl, or $R_{15}$ and $R_{16}$, together with the nitrogen atom linking them, form an unsubstituted or substituted 5-, 6- or 7-membered ring which may contain further hetero atoms.

5. A composition according to claim 1 wherein in formula (2) $R_1$, $R_2$, $R_3$, $R_4$ signify H, OH, —$NR_{15}R_{16}$, —$NR_{15}R_{16}R_{17}$, or $C_1$-$C_{18}$alkyl, s is 1, $R_5$ denotes H, $R_6$ denotes H, methyl or OH, A denotes

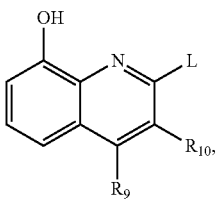

$R_9$, $R_{10}$ are each independently of the other hydrogen, OH, unsubstituted or substituted $C_1$-$C_{18}$alkyl, unsubstituted or substituted phenyl, —$NR_{15}R_{16}$ or —$N^{\oplus}R_{15}R_{16}R_{17}$ and $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

6. A composition according to claim 1 wherein formula (2) is of formula (2a)

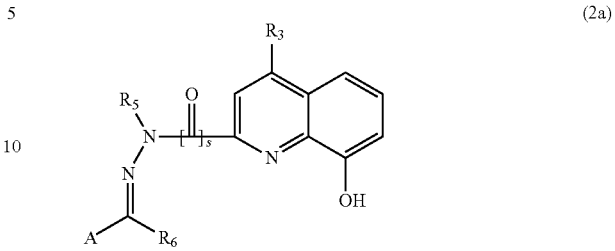

(2a)

wherein $R_3$ is H or OH;

s is 1;

$R_5$ denotes H;

$R_6$ denotes A, H, methyl or OH;

A denotes

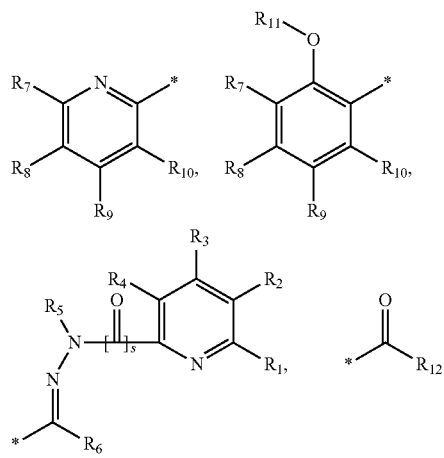

or

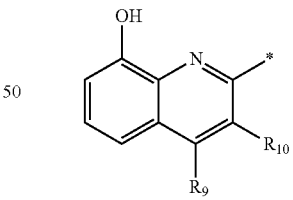

wherein $R_7$, $R_8$, $R_9$, $R_{10}$, $R_{11}$ and $R_{12}$ are each independently of the other hydrogen, OH, unsubstituted or substituted $C_1$-$C_{18}$alkyl, unsubstituted or substituted phenyl, —$NR_{15}R_{16}$ or —$N^{\oplus}R_{15}R_{16}R_{17}$ and $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

7. A composition according to claim 6 wherein in formula (2a)

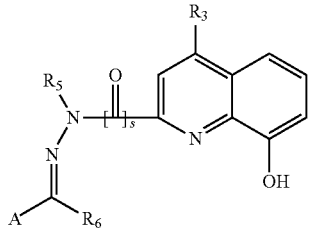

R₃ is H or OH;
s is 1,
R₅ denotes H;
R₆ denotes A, H, methyl or OH;
A denotes

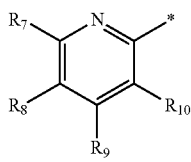

or

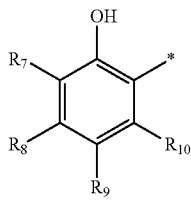

or

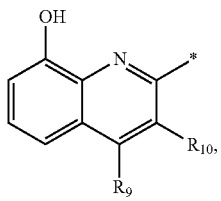

R₇, R₈, R₉, R₁₀ are each independently of the other hydrogen, OH, unsubstituted or substituted C₁-C₈alkyl, unsubstituted or substituted phenyl, —NR₁₅R₁₆ or —N⁺R₁₅R₁₆R₁₇ and R₁₅, R₁₆ and R₁₇ are each independently of the other(s) hydrogen or unsubstituted or substituted C₁-C₁₈alkyl or unsubstituted or substituted phenyl, or R₁₅ and R₁₆, together with the nitrogen atom linking them, form an unsubstituted or substituted 5-, 6- or 7-membered ring which may contain further hetero atoms.

8. A composition according to claim 1 wherein formula (2) is of formula (2b), (2c) or (2d)

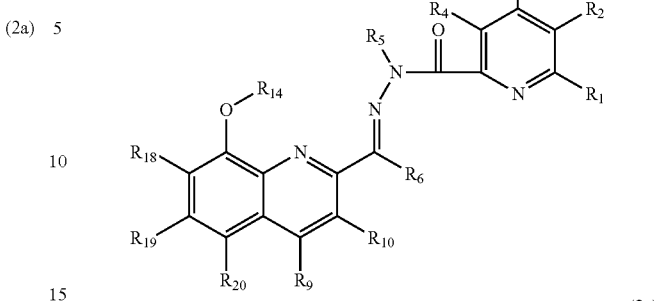

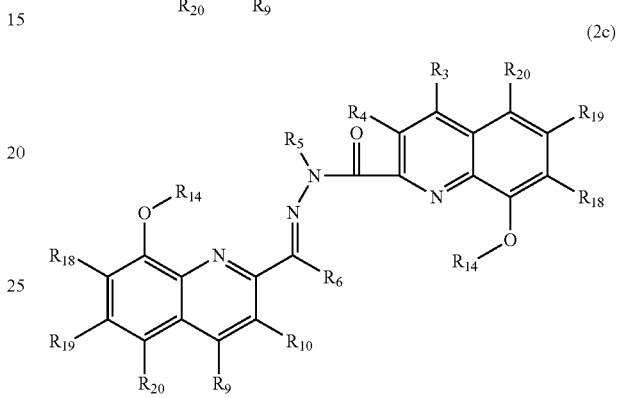

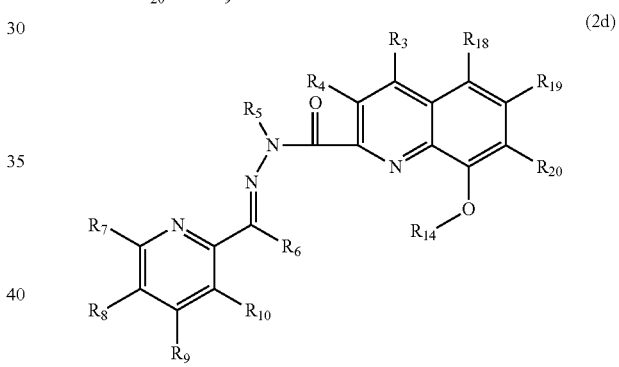

wherein
R₁, R₂, R₃, R₄ signify H, OH, —NR₁₅R₁₆ or —N⁺R₁₅R₁₆R₁₇ or C₁-C₁₈alkyl, R₅ denotes H, R₆ denotes H, OH, C₁-C₁₈alkyl or unsubstituted or substituted phenyl;

R₇, R₈, R₉, R₁₀ are each independently of the other hydrogen, OH, unsubstituted or substituted C₁-C₈alkyl, unsubstituted or substituted phenyl, —NR₁₅R₁₆ or —N⁺R₁₅R₁₆R₁₇;

R₁₅, R₁₆ and R₁₇ are each independently of the other(s) hydrogen or unsubstituted or substituted C₁-C₁₈alkyl or unsubstituted or substituted phenyl, or R₁₅ and R₁₆, together with the nitrogen atom linking them, form an unsubstituted or substituted 5-, 6- or 7-membered ring which may contain further hetero atoms, R₁₄ is hydrogen or unsubstituted or substituted C₁-C₁₈alkyl or unsubstituted or substituted phenyl and R₁₈, R₁₉ and R₂₀ are independently of each other hydrogen, unsubstituted or substituted C₁-C₁₈alkyl or unsubstituted or substituted phenyl, cyano, halogen, nitro, —OH, —COOR₁₃ or —SO₃R₁₃ wherein R₁₃ is hydrogen, a cation or unsubstituted or substituted C₁-C₁₈alkyl or unsubstituted or substituted aryl;

or $R_{18}$, $R_{19}$ and $R_{20}$ are —$SR_{14}$, —$SO_2R_{14}$ or —$OR_{14}$ wherein $R_{14}$ is hydrogen or unsubstituted or substituted $C_1$-$C_{18}$alkyl or unsubstituted or substituted aryl;

or $R_{18}$, $R_{19}$ and $R_{20}$ are —$NR_{15}R_{16}$, —($C_1$-$C_6$alkylene)-$NR_{15}R_{16}$, —$N^{\oplus}R_{15}R_{16}R_{17}$, —($C_1$-$C_6$alkylene)-$N^{\oplus}R_{15}R_{16}R_{17}$, —$N(R_{14})$—($C_1$-$C_6$alkylene)-$NR_{15}R_{16}$, —$N[(C_1$-$C_6$alkylene)-$NR_{15}R_{16}]_2$, —$N(R_{14})$—($C_1$-$C_6$alkylene)-$N^{\oplus}R_{15}R_{16}R_{17}$, —$N[(C_1$-$C_6$alkylene)-$N^{\oplus}R_{15}R_{16}R_{17}]_2$, —$N(R_{14})$—$N$—$R_{15}R_{16}$ or —$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

9. A granule comprising
a) from 1-99 wt-%, based on the total weight of the granule, of at least one metal complex compound of formula (1) as defined in claim 1 and of at least one peroxide,
b) from 1-99 wt-%, based on the total weight of the granule, of at least one binder selected from the group consisting of water-soluble, dispersible or water-emulsifiable anionic dispersants, non-ionic dispersants, polymers, and waxes,
c) from 0-20 wt-%, based on the total weight of the granule, of at least one encapsulating material,
d) from 0-20 wt-%, based on the total weight of the granule, of at least one further additive and
e) from 0-20 wt-% based on the total weight of the granule, of water.

10. A compound of formula (2b), (2c) or (2d)

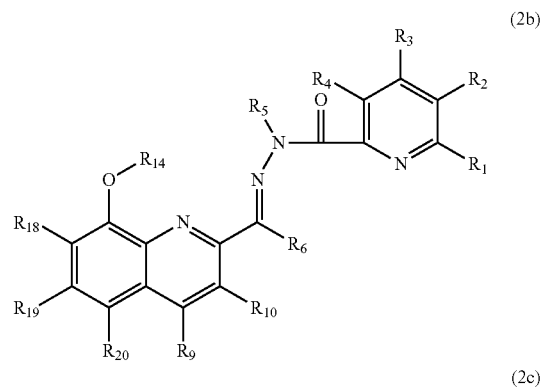

(2b)

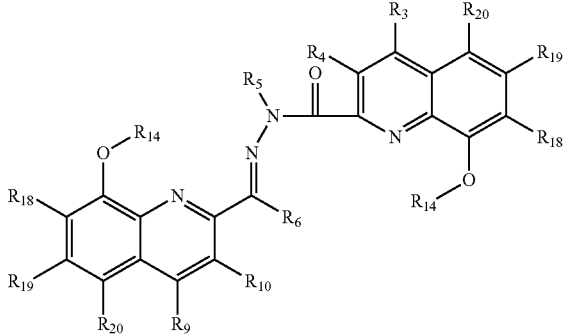

(2c)

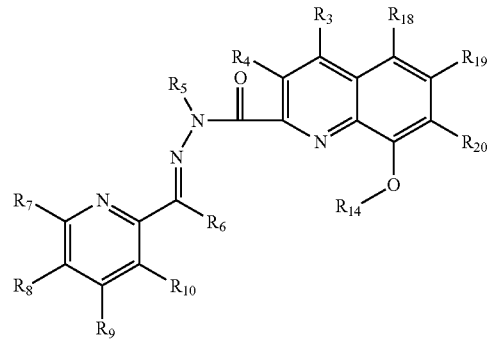

(2d)

wherein $R_1$, $R_2$, $R_3$, $R_4$ signify H, OH, —$NR_{15}R_{16}$, —$N^{\oplus}R_{15}R_{16}R_{17}$, or $C_1$-$C_{18}$alkyl, $R_5$ denotes H, $R_6$ denotes H, OH, $C_1$-$C_{18}$alkyl or unsubstituted or substituted phenyl;

$R_7$, $R_8$, $R_9$, $R_{10}$ are each independently of the other hydrogen, OH, unsubstituted or substituted $C_1$-$C_8$alkyl, unsubstituted or substituted phenyl, —$NR_{15}R_{16}$ or —$N^{\oplus}R_{15}R_{16}R_{17}$;

$R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms;

$R_{14}$ is hydrogen or unsubstituted or substituted $C_1$-$C_{18}$alkyl or unsubstituted or substituted phenyl and $R_{18}$, $R_{19}$ and $R_{20}$ are independently of each other hydrogen, unsubstituted or substituted $C_1$-$C_{18}$alkyl or unsubstituted or substituted phenyl, cyano, halogen, nitro, —OH, —$COOR_{13}$ or —$SO_3R_{13}$ wherein $R_{13}$ is hydrogen, a cation or unsubstituted or substituted $C_1$-$C_{18}$alkyl or unsubstituted or substituted aryl;

or $R_{18}$, $R_{19}$ and $R_{20}$ are —$SR_{14}$, —$SO_2R_{14}$ or —$OR_{14}$ wherein $R_{14}$ is hydrogen or unsubstituted or substituted $C_1$-$C_{18}$alkyl or unsubstituted or substituted aryl;

or $R_{18}$, $R_{19}$ and $R_{20}$ are —$NR_{15}R_{16}$, —($C_1$-$C_6$alkylene)-$NR_{15}R_{16}$, —$N^{\oplus}R_{15}R_{16}R_{17}$, —($C_1$-$C_6$alkylene)-$N^{\oplus}R_{15}R_{16}R_{17}$, —$N(R_{14})$—($C_1$-$C_6$alkylene)-$NR_{15}R_{16}$, —$N[(C_1$-$C_6$alkylene)-$NR_{15}R_{16}]_2$, —$N(R_{14})$—($C_1$-$C_6$alkylene)-$N^{\oplus}R_{15}R_{16}R_{17}$, —$N[(C_1$-$C_6$alkylene)-$N^{\oplus}R_{15}R_{16}R_{17}]_2$, —$N(R_{14})$—$N$—$R_{15}R_{16}$ or —$N(R_{14})$—$N^{\oplus}R_{15}R_{16}R_{17}$, wherein $R_{14}$ is as defined above and $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms.

11. A compound of formula (2b), (2c) or (2d) according to claim 10 wherein $R_1$, $R_2$, $R_3$, $R_4$ signify H, OH, —$NR_{15}R_{18}$, —$N^{\oplus}R_{15}R_{16}R_{17}$ or $C_1$-$C_{18}$alkyl, $R_5$ denotes H, $R_6$ denotes H, OH, $C_1$-$C_4$alkyl or phenyl;

$R_7$, $R_8$, $R_9$, $R_{10}$ are each independently of the other hydrogen, OH, unsubstituted or substituted $C_1$-$C_8$alkyl, unsubstituted or substituted phenyl, —$NR_{15}R_{16}$ or —$N^{\oplus}R_{15}R_{16}R_{17}$, $R_{15}$, $R_{16}$ and $R_{17}$ are each independently of the other(s) hydrogen or unsubstituted or substituted $C_1$-$C_{18}$alkyl or unsubstituted or substituted phenyl, or $R_{15}$ and $R_{16}$, together with the nitrogen atom linking them, form an unsubstituted or substituted 5-, 6- or 7-membered ring which may contain further hetero atoms;

$R_{14}$ is hydrogen or $C_1$-$C_4$alkyl or phenyl; and $R_{18}$, $R_{19}$ and $R_{20}$ are independently of each other hydrogen, $C_1$-$C_{18}$alkyl, phenyl, cyano, halogen, nitro, —OH, —COOR$_{13}$ or —SO$_3$R$_{13}$ wherein $R_{13}$ is hydrogen or an alkali metal cation;

or $R_{18}$, $R_{19}$ and $R_{20}$ are —SR$_{14}$, —SO$_2$R$_{14}$ or —OR$_{14}$ wherein $R_{14}$ hydrogen or $C_1$-$C_4$alkyl.

12. A metal complex of formula (1)

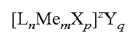 (1)

wherein
Me is manganese, titanium, iron, cobalt, nickel or copper,
X is a coordinating or bridging radical,
n and m are each independently of the other an integer having a value of from 1 to 8,
p is an integer having a value of from 0 to 32,
z is the charge of the metal complex,
Y is a counter-ion,
q=z/(charge of Y) and
L is a ligand of formula (2b), (2c) or (2d) according to claims 10.

* * * * *